United States Patent [19]

Urban

[11] Patent Number: 4,876,367
[45] Date of Patent: Oct. 24, 1989

[54] MACROCYCLIC POLYETHER CARBOXYLIC ACIDS

[75] Inventor: Frank J. Urban, Waterford, Conn.
[73] Assignee: Pfizer Inc., New York, N.Y.
[21] Appl. No.: 241,169
[22] Filed: Sep. 6, 1988

Related U.S. Application Data

[62] Division of Ser. No. 916,676, Sep. 4, 1986, Pat. No. 4,777,270.

[51] Int. Cl.$^4$ ............................................ C07D 323/00
[52] U.S. Cl. ...................................... 549/349; 549/351
[58] Field of Search .................. 549/349, 351; 514/450

[56] References Cited

U.S. PATENT DOCUMENTS

| | | | |
|---|---|---|---|
| 3,580,889 | 5/1971 | Barney et al. | 260/47 |
| 3,622,577 | 11/1971 | Pedersen | 260/248 |
| 3,686,225 | 8/1972 | Pedersen | 260/340.3 |
| 3,687,978 | 8/1972 | Pedersen | 260/340.3 |
| 3,839,557 | 10/1974 | Raun | 424/115 |
| 3,965,116 | 6/1976 | Cram | 260/338 |
| 3,997,565 | 12/1976 | Kauer | 260/340.3 |
| 4,072,693 | 2/1978 | Reinhoudt et al. | 260/338 |
| 4,104,275 | 8/1978 | Kauer | 260/297 |
| 4,152,335 | 5/1979 | Reinhoudt et al. | 260/338 |
| 4,186,175 | 1/1980 | Tomaja | 204/158 |

FOREIGN PATENT DOCUMENTS

| | | |
|---|---|---|
| 0644789 | 1/1979 | U.S.S.R. |
| 0732270 | 5/1980 | U.S.S.R. |
| 0981318 | 12/1982 | U.S.S.R. |

OTHER PUBLICATIONS

Chemical Abstracts, vol. 87, 200604h (1977).
Chemical Abstracts, vol. 85, 46618r (1976).
Chemical Abstracts, vol. 85, 123893f (1976).
Chemical Abstracts, vol. 83, 192012p (1975).
Chemical Abstracts, vol. 96, 142822a (1982).
Chemical Abstracts, vol. 91, 107964y (1979).
Newcomb et al., J. Amer. Chem. Soc., vol. 97:5, 1257–1259 (1975).
Pedersen, C. J., J. Amer. Chem. Soc., vol. 92:2, 391–394 (1970).
Pedersen, C. J., Federation Proceedings, vol. 27, No. 6, 1305–1309 (1968).
Pedersen et al., Angew. Chem. Internat. Edit., vol. 11, 16–25 (1972).
Blair et al., J. Chem. Soc., Perkin I, No. 3, 245–250 (1975).
Opella et al., J. Am. Chem. Soc., vol. 96 (22), 1974, pp. 7159–7160.
Bell et al., J. Am. Chem. Soc., vol. 104 (19), 1982, pp. 5185–5188.

*Primary Examiner*—Glennon H. Hollrah
*Assistant Examiner*—Ba K. Trinh
*Attorney, Agent, or Firm*—Peter C. Richardson; J. Trevor Lumb

[57] ABSTRACT

A series of novel, macrocyclic polyether compounds. The macrocycles have a 21-membered ring, containing six oxygen atoms, and they have a carboxy group (or a salt thereof) directed towards the interior of the ring. Administration of the compounds of the invention to ruminant animals (e.g. cattle and sheep) modifies their digestive fermentation processes such that the volatile fatty acids produced in the rumen contain a higher proportion of propionates rather than acetates, thereby increasing the efficiency of feed utilization in said ruminant animals. Additionally, the compounds of the invention show antibacterial activity in vitro against certain gram-positive microorganisms.

10 Claims, No Drawings

MACROCYCLIC POLYETHER CARBOXYLIC ACIDS

CROSS-REFERENCE TO RELATED APPLICATION

This application is a division of application Ser. No. 916,676, filed Sept. 4, 1986, now U.S. Pat. No. 4,777,270.

TECHNICAL FIELD

The efficiency of feed utilization in domestic animals, especially the ruminants such as cattle and sheep, is of economic importance in the farming industry. For this reason, attempts have been made to increase the efficiency with which ruminants utilize their food.

As an aid to discovering methods of increasing the efficiency of feed utilization in ruminants, studies on the biochemical mechanisms by which ruminants digest and degrade food, particularly carbohydrates, has been widely studied. It is now known that carbohydrates are degraded in the rumen to monosaccharides, which are converted to pyruvates, and thence to acetates and propionates. Additionally acetates recombine in the rumen to some extent to form butyrates. These acetates, propionates and butyrates, collectively known as volatile fatty acids (or VFA's), are all used as energy sources by ruminants. However, the conversion of pyruvates to acetates involves chain-shortening by one carbon atom, and this carbon atom is lost in the form of methane gas. Thus the production of propionates from carbohydrates in the rumen of ruminant animals represents a more energy-efficient degradative pathway than the production of acetates and butyrates.

As a result, treatment of a ruminant so as to cause a shift in VFA ratios in the rumen towards increased rumen propionic acid (RPA) leads to a beneficial effect on ruminant growth for a given amount of food consumption. Thus there is increased efficiency of feed utilization.

BACKGROUND ART

Several, naturally-occuring, polyether antibiotics (e.g. monensin) have been reported to increase feed utilization in ruminants; U.S. Pat. No. 3,839,557. A variety of macrocyclic polyether compounds having a carboxy group directed into the polyether ring have been described in U.S. Pat. No. 3,965,116 and *Journal of the American Chemical Society*, 97, 1257 (1975), but none of these compounds was reported to have feed utilization efficiency increasing properties.

DISCLOSURE OF INVENTION

This invention provides a series of new chemical compounds which increase rumen propionic acid production in ruminant animals when administered orally to ruminants, at a low level, daily. These new chemical compounds are macrocyclic polyether compounds, which have a 21-membered ring, containing six oxygen atoms, and also have a carboxy group directed towards the interior of the polyether ring.

More particularly, this invention provides a novel macrocyclic polyether compound selected from the group consisting of

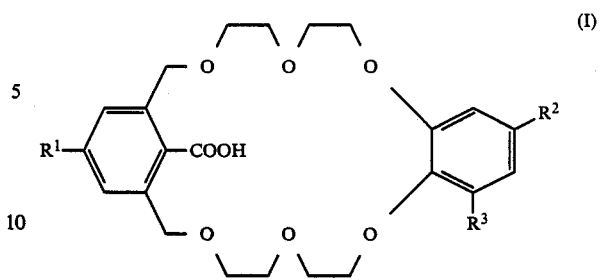

and

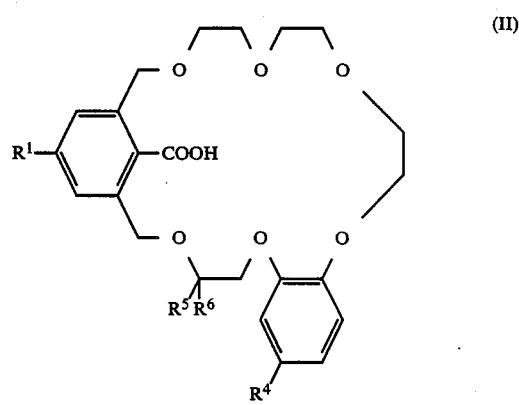

and the pharmaceutically-acceptable base salts thereof, wherein:

-$R^1$ is selected from the group consisting of hydrogen and t-butyl;

$R^2$ is selected from the group consisting of hydrogen, alkyl having 1 to 14 carbons, cycloalkyl having 5 to 8 carbons, phenyl, alkylphenyl having 1 to 4 carbons in said alkyl, 1-adamantyl, —C($R^7$)=CH—C(CH$_3$)$_3$,

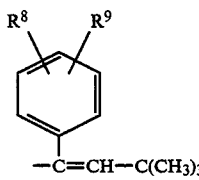 and 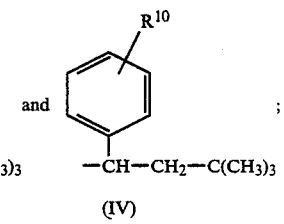 ;

(III) (IV)

wherein $R^7$ is hydrogen or alkyl having 1 to 8 carbons; $R^8$ and $R^9$ when taken separately are each hydrogen, alkyl having 1 to 3 carbons, alkoxy having 1 to 3 carbons or alkylthio having 1 to 3 carbons; $R^8$ and $R^9$ when taken together with the carbons to which they are attached form a fused benzo ring; and $R^{10}$ is hydrogen, alkyl having 1 to 3 carbons, alkoxy having 1 to 3 carbons or alkylthio having 1 to 3 carbons;

$R^3$ is selected from the group consisting of hydrogen, alkyl having 1 to 8 carbons, hydroxymethyl, methoxymethyl,

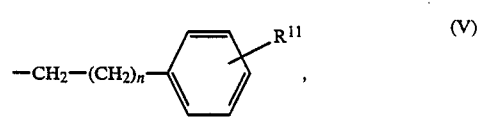

-continued

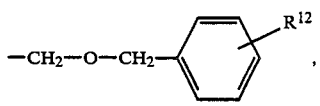

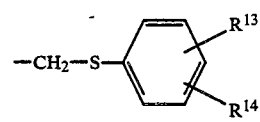

and

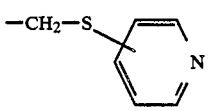

wherein R¹¹ is hydrogen, alkyl having 1 to 3 carbons, fluoro or chloro; R¹² is hydrogen, alkyl having 1 to 3 carbons or alkylthio having 1 to 3 carbons; n is an integer from 0 to 3; and R¹³ and R¹⁴ are each hydrogen, alkyl having 1 to 3 carbons, alkoxy having 1 to 3 carbons, alkylthio having 1 to 3 carbons, fluoro, chloro, bromo, hydroxy, acetyl, acetamido, benzoyl or trifluoromethyl;

R⁴ is selected from the group consisting of hydrogen and alkyl having 1 to 8 carbons;

and either R⁵ is hydrogen and R⁶ is selected from the group consisting of hydrogen, alkyl having 1 to 8 carbons, phenoxymethyl, chlorophenoxymethyl, 4-t-butylphenoxymethyl and thiophenoxymethyl; or R⁵ and R⁶ when taken together with the carbon atom to which they are attached form a cyclopentylidene, cyclohexylidene, 4-phenylcyclohexylidene, 4-t-butylcyclohexylidene, 3,3,5-trimethylcyclohexylidene or cycloheptylidene group;

provided that when R³ is said

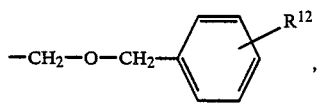

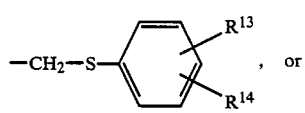

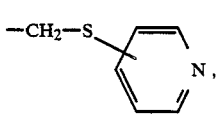

R² must be t-octyl.

Said compounds of the formula I and II are useful for administration to ruminant animals, e.g. cattle and sheep, for the purpose of increasing the efficiency of feed utilization. Additionally said compounds of formula I and II are active as antibacterial agents in vitro against certain gram-positive microorganisms, e.g. *Staphylococcus aureus*.

A first preferred group of compounds of this invention consists of the compounds of formula I, wherein R¹ is t-butyl, R² is t-octyl and R³ is hydrogen or said alkyl.

A second preferred group of compounds of this invention consists of the compounds of formula I, wherein R¹ is t-butyl, R² is said —C(R⁷)═CH—C(CH₃)₃ or said

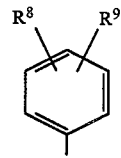

and R³ is said alkyl.

A third preferred group of compounds of this invention consists of the compounds of formula I, wherein R¹ is t-butyl, R² is t-octyl and R³ is said

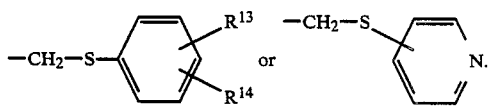

Especially valuable individual compounds of the invention are: (a) the compound of formula I, wherein R¹ is t-butyl, R² is t-octyl and R³ is methyl; and (b) the compound of formula I, wherein R¹ is t-butyl, R² is t-octyl and R³ is thiophenoxymethyl.

DETAILED DESCRIPTION

This invention relates to the new chemical compounds of formulas I and II. These are large-ring (21-membered) polyether compounds, and the large ring further incorporates two aromatic fragments, one a 1,3-disubstituted benzene ring and the other a 1,2-disubstituted benzene ring. Moreover, these benzene rings can carry substituents and in general substituents which increase the lipophilicity of the parent macrocycle are desirable for imparting feed utilization efficiency increasing properties. For example, these substituents can be straight- or branched-chain alkyl groups, and particular alkyl groups which are commonly used are the tertiary butyl (t-butyl) group and the group of the formula —C(CH₃)₂—CH₂—C(CH₃)₃. The latter group is named systematically as the 1,1,3,3-tetramethylbutyl group; however, for convenience in this specification, this group is referred to by its trivial name, t-octyl.

The compounds of formula I and II are usually obtained by hydrolysis of the corresponding ester compound of the formula

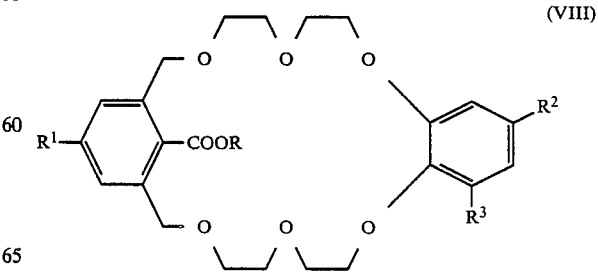

or

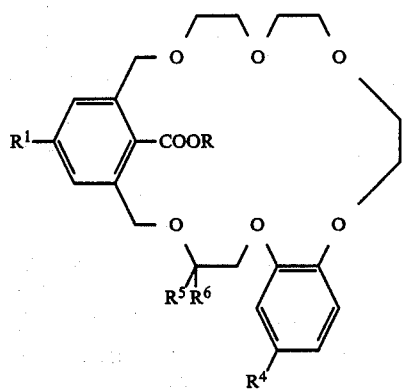

(IX)

wherein $R^1$, $R^2$, $R^3$, $R^4$, $R^5$ and $R^6$ are as defined previously, and R is a lower-alkyl group (e.g. an alkyl having 1 to 5 carbons), by basic hydrolysis. Favorably, R is methyl. This ester hydrolysis reaction can be carried out by treating said compound of the formula VIII or IX with water at a pH between 9 and 12, optionally in the presence of a co-solvent. In practice, it is conveniently carried out by treating the compound of formula VIII or IX with from about 1 to about 20 molar equivalents, and preferably about 2 to 5 molar equivalents, of an alkali metal hydroxide or alkaline earth metal hydroxide, in a mixture of water and a water-miscible, volatile, organic co-solvent. Typical co-solvents which can be used are lower-alkanols such as methanol and ethanol; glycols such as ethylene glycol and propylene glycol; and water-miscible, low-molecular weight ethers such as tetrahydrofuran and 1,2-dimethoxyethane. Usually, a large excess of water is used on molar basis, and sufficient co-solvent is added to give a homogeneous hydrolysis medium. Preferred basic agents for the hydrolysis reaction are the hydroxides of sodium and potassium.

Hydrolysis of an ester of formula VIII or IX is usually carried out at a temperature between 25° and 120° C., and preferably about 60° to 80° C. Reaction times vary according to a variety of factors, such as temperature and concentration of the reaction medium, but usually reaction times ranging from several hours (e.g. six hours) to several days (e.g. three days) are needed for the reaction to proceed substantially to completion.

At the end of the hydrolysis reaction, the organic co-solvent is usually removed by evaporation in vacuo, and the residual aqueous phase is extracted with a volatile, water-immiscible, organic solvent such as chloroform or dichloromethane. Evaporation of the organic extract then affords the required compound of formula I or II in the form of a carboxylate salt, where the cation corresponds to the alkali or alkaline earth metal used during the hydrolysis reaction. Alternatively, after removal of the organic co-solvent at the end of the hydrolysis reaction, the residual aqueous phase can be acidified (e.g. to a pH below about 3) before extraction with the water-immiscible, organic solvent. Evaporation of the extract then affords the compound I or II in the form of its free acid.

A compound of the formula I or II can be purified, if desired, by standard methods, such as recrystallization or chromatography.

An ester of the formula VIII or IX can be prepared by coupling a benzoate ester of the formula

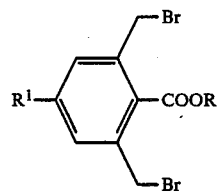

(X)

wherein R and $R^1$ are as defined previously, with a diol of the formula

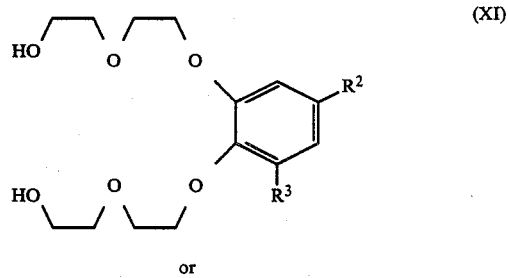

(XI)

or

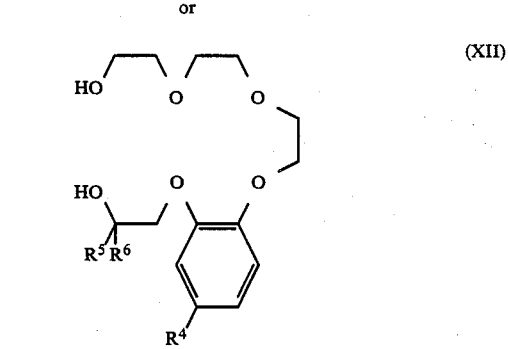

(XII)

wherein $R^2$, $R^3$, $R^4$, $R^5$ and $R^6$ are as defined previously.

Coupling between a benzoate ester of the formula X and a diol of the formula XI or XII is usually achieved by contacting the reactants in a reaction-inert solvent in the presence of a strong, non-nucleophilic base. In a typical procedure, a tetrahydrofuran solution containing substantially equimolar amounts of a compound of the formula X and a diol of the formula XI or XII is added dropwise to a suspension of sodium hydride (2.2 molar equivalents) in refluxing tetrahydrofuran. The reaction mixture is then heated under reflux for a few hours, e.g. two to 10 hours, to complete the reaction. The excess of sodium hydride is decomposed by the careful addition of water (usually in the form of wet tetrahydrofuran) and the organic solvent is removed by evaporation in vacuo. The product is extracted into a volatile, water-immiscible organic solvent (e.g. dichloromethane) and removal of the solvent in vacuo then affords the crude product of formula VIII or IX. The crude product is usually purified by column chromatography on silica gel.

The diols of the formula XI, wherein $R^2$ is selected from the group consisting of hydrogen, alkyl having 1 to 14 carbons, cycloalkyl having 5 to 8 carbons, phenyl, alkylphenyl having 1 to 4 carbons in said alkyl and 1-adamantyl; and $R^3$ is as defined previously can be prepared from the corresponding catechol of the formula

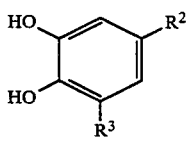
(XIII)

This involves a two-step procedure. In the first step, the catechol of the formula XIII is dialkylated with 2-(2-[2-tetrahydropyranyloxy]ethoxy)ethyl chloride, the compound of the formula

(XIV)

wherein "THP" represents the 2-tetrahydropyranyl group, to give the diprotectected diol of the formula

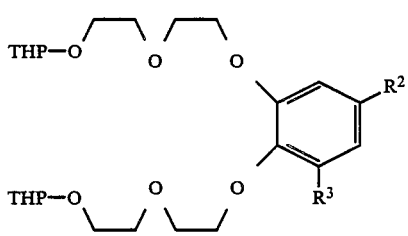
(XV)

followed in the second step by removal of the THP protecting groups. Both of these reactions are classical transformations which are carried out by standard methods. Alkylation of the catechol XIII is usually carried out by treatment with about 2.2 molar equivalents of the chloro compound of formula XIV in the presence of an excess of potassium carbonate in N,N-dimethylformamide solution at about 140° C. for several hours. At the end of the reaction, the reaction mixture is diluted with water and the compound of formula XV can be recovered by extraction into a volatile, water-immiscible, organic solvent followed by evaporation of the solvent. The THP protecting groups are removed by treatment with an excess of 1N hydrochloric acid in methanol solution at room temperature for about one hour. Removal of the solvent by evaporation in vacuo affords the diol of formula XI. The diol of the formula XI can be coupled directly with the compound of the formula X; alternatively, it can be purified by standard methods, if desired.

The diols of the formula XI, wherein $R^2$ is selected from the group consisting of —C($R^7$)=CH—C(CH$_3$)$_3$,

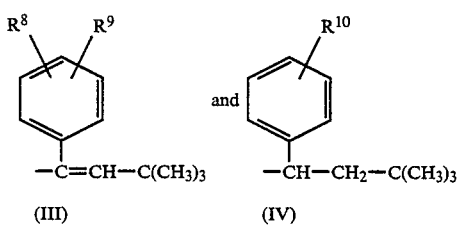

wherein $R^8$, $R^9$ and $R^{10}$ are as defined previously, and $R^3$ is as defined previously other than formula VII or VIIA, can be prepared from the requisite ketone of the formula

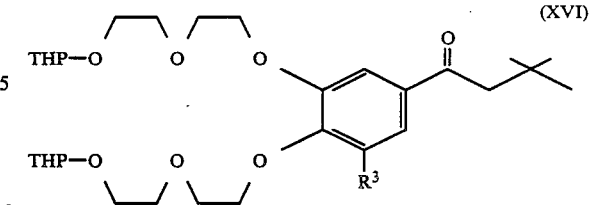
(XVI)

In order to obtain a diol of formula XI, wherein $R^2$ is —C($R^7$)=CH—C(CH$_3$)$_3$, the appropriate compound of formula XVI is reduced with sodium borohydride followed by treatment with acid. The borohydride reduction is carried out by standard methods. For example, a solution of the ketone of formula XVI in a lower-alkanol, e.g. methanol, is treated with an excess of solid sodium borohydride at a temperature from 0° to 30° C., and usually at room temperature. Reaction takes place quite smoothly and quickly, and at room temperature it is normally complete within 1 to 2 hours. The reduction product is then treated with acid in the same manner described for treatment of a compound of formula XV with acid, to give the required diol of formula XI, wherein $R^2$ is —C($R^7$)=CH—C(CH$_3$)$_3$.

In order to obtain a diol of formula XI, wherein $R^2$ is of formula III, the appropriate ketone of formula XVI is reacted with the requisite Grignard reagent of formula

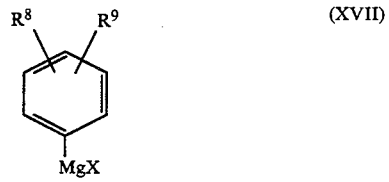
(XVII)

wherein X is chloro or bromo and $R^8$ and $R^9$ are as defined previously, followed by treatment with acid. The Grignard reaction is usually carried out by treating the ketone of formula XVI with about 2 molar equivalents of the Grignard reagent in an ether solvent (e.g. diethyl ether or tetrahydrofuran) at room temperature. The reaction is allowed to proceed for several hours, e.g. overnight, and then it is worked-up in standard fashion. The product of this Grignard reaction is treated with acid in the same manner described for treatment of a compound of formula XV with acid, to give the required diol of formula XI, wherein $R^2$ is of formula III.

In order to obtain a diol of the formula XI, wherein $R^2$ is of formula IV, the appropriate ketone of formula XVI is reacted with the requisite Grignard reagent of the formula

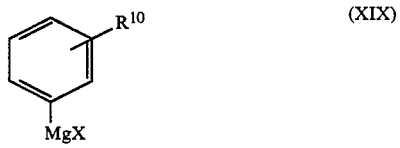
(XIX)

followed by hydrogenation of the product of the Grignard reaction, followed by treatment with acid. The Grignard reaction and the treatment with acid are carried out as described for preparation of a diol of formula XI, wherein $R^2$ is of formula III. The hydrogenation step can be carried out in ethanol solution, at room temperature, at a pressure from 1 to 4 kg/cm², over a palladium-on-carbon catalyst, according to standard procedures.

The ketone of the formula XVI can be prepared from the appropriate catechol of the formula

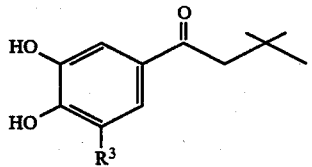
(XX)

by dialkylation with 2-(2-[2-tetrahydropyranyloxy]ethoxy)ethyl chloride (XIV) in the same manner described earlier for dialkylation of a catechol of formula XIII.

Many of the simple catechols of the formula XIII, wherein R² is alkyl, cycloalkyl, phenyl, alkylphenyl or 1-adamantyl, and R³ is as previously defined, are known compounds, which can be made by the known methods, or analogs, which, can be prepared by analogous procedures. Thus, the R² substituent can often be introduced into a catechol of the formula

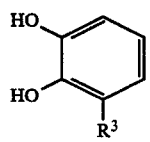
(XXI)

or its dimethyl ether, by acid catalyzed reaction with an olefin or an alcohol, or by Friedel-Crafts alkylation using an alkyl halide, followed if necessary by demethylation, e.g.

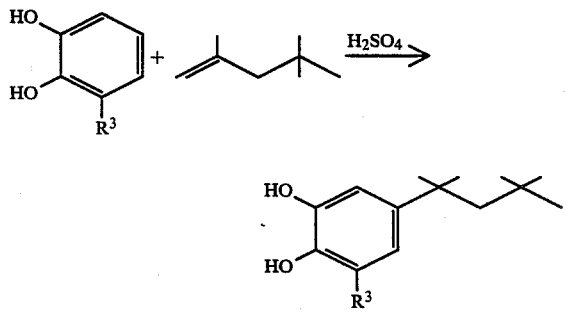

See further J. Jelinek, Chem. Primsyl, 9, 398 (1959); Chem. Abs., 54, 8691i (1960).

Several catechols of the formula XXI, wherein R³ is of the formula V, can be prepared, for example, from 2,3-dimethoxybenzaldehyde, viz:

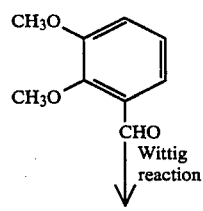
Wittig reaction

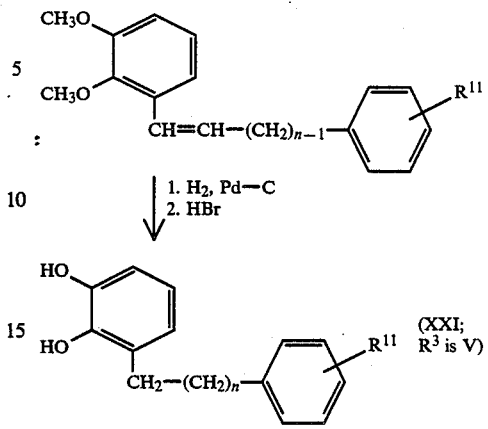

These transformations are carried out by standard methods, well-known in the art.

The catechols of the formula XX can be prepared from the appropriate catechol of the formula XXI by acylation with 3,3-dimethylbutyryl chloride, to give the diester of the formula XXII, followed by heating with aluminum chloride in carbon disulfide (the Fries rearrangement), viz:

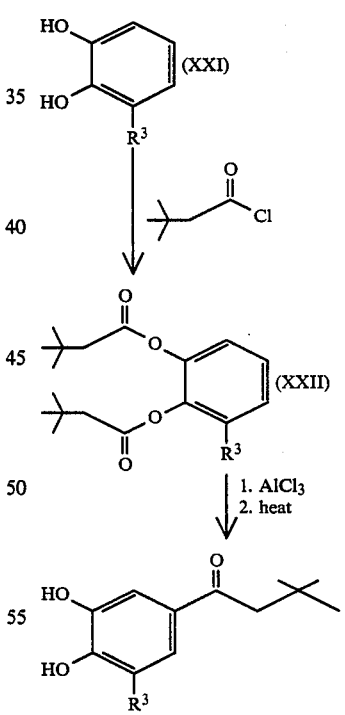

according to standard procedures.

Catechols of the formula XIII, wherein R² is t-octyl and R³ is of the formula VII or VIIA, can be prepared from 4-t-octylcatechol by a Mannich reaction with paraformaldehyde and morpholine, to give the morpholinomethyl compound XXIII, followed by reaction with the appropriate thiol, viz:

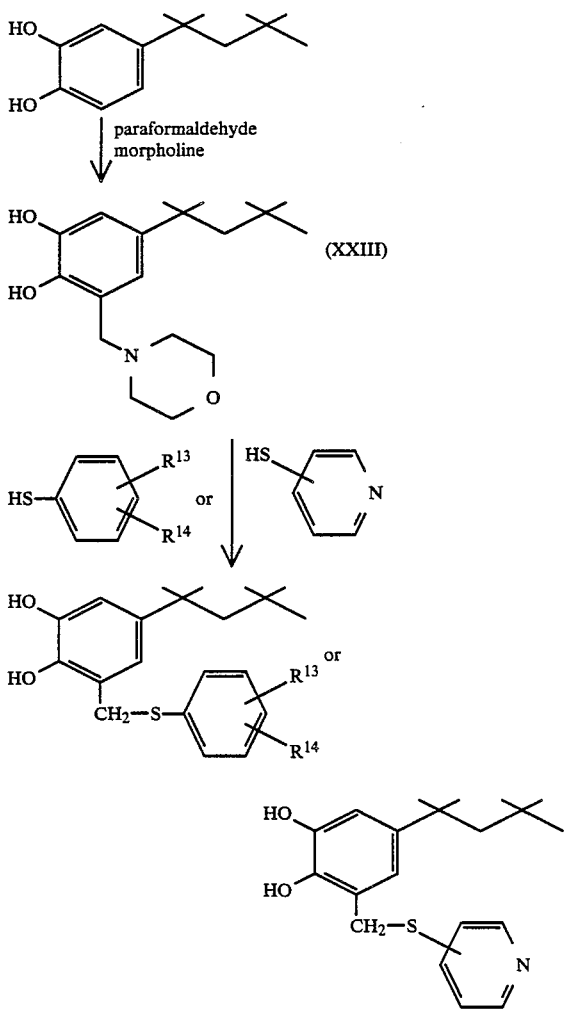

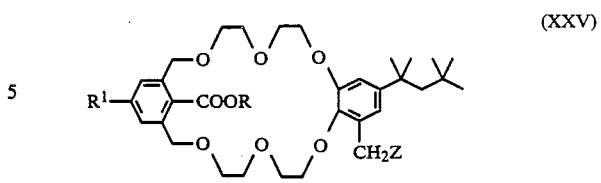

wherein Z is hydroxy. The alcohol XXV can be reacted with phosphorus tribromide and with thionyl chloride, to give the corresponding compounds in which Z is Br and Cl, respectively. The latter halo compounds react with thiophenols of the formula $HS-C_6H_3R^{13}R^{14}$ or a pyridinethiol to give the corresponding compound of the formula VIII, wherein $R^1$ is hydrogen or t-butyl, $R^2$ is t-octyl and $R^3$ is said radical of formula VII or VIIA. Further, the benzyl alcohol of the formula XXV, wherein Z is hydroxy, can be reacted with sodium hydride and a benzyl halide of the formula $W-CH_2-C_6H_4-R^{12}$, wherein W is chloro or bromo to give the macrocycle of the formula VIII, wherein $R^1$ is hydrogen or t-butyl, $R^2$ is t-octyl and $R^3$ is the radical of formula VI.

The diols of the formula XII can be prepared from the appropriate diol of the formula

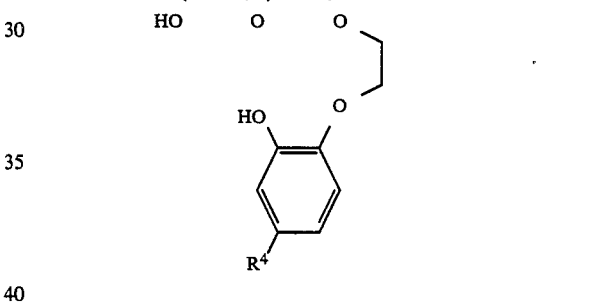

by reaction with an epoxide of the formula

The reaction is normally carried out simply by contacting substantially equimolar quantities of the compounds of formula XXVI and XXVII with a molar equivalent amount of potassium carbonate, at elevated temperature, in the absence of solvent. Temperatures in the range from 90° to 150° C., and preferably about 120° C., are normally used, and reaction times of several hours, e.g., 20 hours, are usually required. The crude product is usually sufficiently pure for reaction with a benzoate ester of formula X.

In one method, the diol of the formula XXVI is obtained by reaction of the requisite catechol of the formula

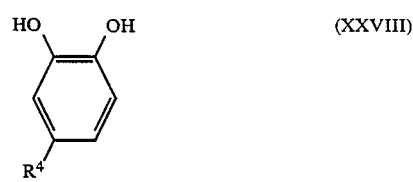

The Mannich reaction can be carried out by standard methods; see further Fields et al., *Journal of Organic Chemistry*, 29, 2640 (1964). Reaction of the Mannich base XXIII with the thiol can be carried out by heating the reactants in a polar organic solvent, such as N,N-dimethylformamide, for several hours at about 80° to 140° C.

Additionally, the Mannich base XXIII can be reacted with 2-(2-[2-tetrahydropyranyloxy]ethoxy)ethyl chloride (XIV), followed by removal of the THP protecting groups with acid, followed by coupling with a benzoate ester (X), by the methods previously described, to give the macrocyclic polyether of the formula XXIV:

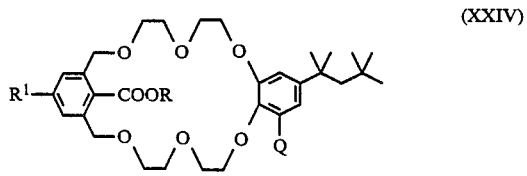

wherein Q is morpholinomethyl. Treatment of macrocycle XXIV with refluxing acetic anhydride followed by column chromatography and mild hydrolysis (ethanolic potassium hydroxide at room temperature) affords the compound of formula XXV with one molar equivalent of the chloro compound of the formula

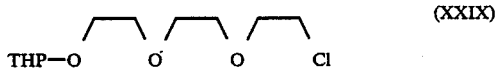

wherein, as before, THP is the 2-tetrahydropyranyl group, followed by treatment with acid to remove the THP group. Reaction of catechol XXVIII with chloro compound XXIX is carried out by the method described earlier for reaction of catechol XIII with chloro compound XIV, while removal of the THP protecting groups is carried out in the same manner described earlier for removal of the THP groups from a compound of formula XV. However, it is usually necessary to purify the intermediate resulting from reaction of catechol XXVIII with chloro compound XXIX by chromatography, since some dialkylated product can be formed, and, when $R^4$ is other than hydrogen, a mixture of mono-alkylated proudcts is usually obtained.

In another method, the diol of the formula XXVI can be obtained from a salicylaldehyde of formula XXXI by Baeyer-Villiger oxidation followed by hydrolysis. The salicylaldehyde of formula XXXI can be obtained from the appropriate salicylate ester of formula XXX or salicylaldehyde of formula XXXA, viz:

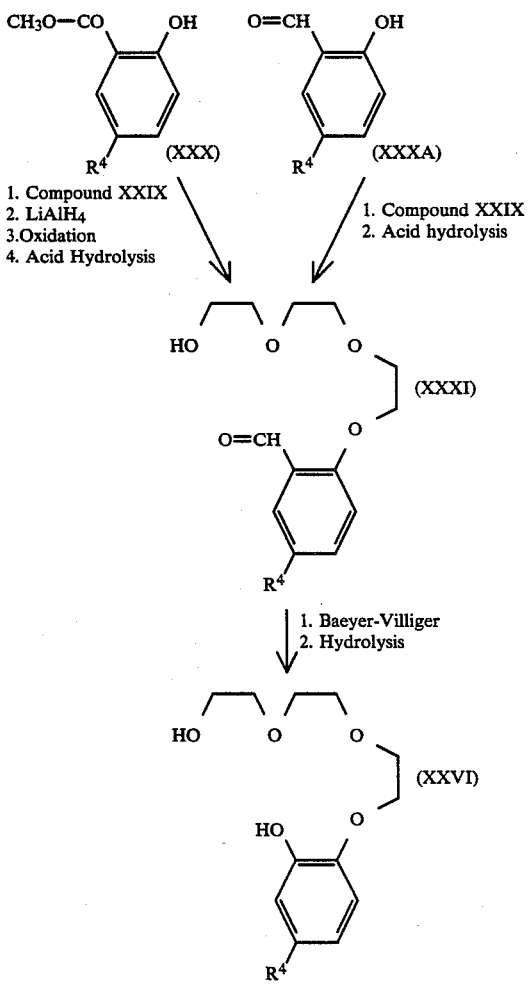

Reaction of salicylaldehyde XXX with chloro compound XXII and acid hydrolysis of the alkylation product are carried out as described previously for reaction of catechol XIII with chloro compound XIV and hydrolysis of compound XV. The Baeyer-Villiger oxidation and hydrolysis are carried out using standard methods for this type of transformation.

The compounds of the formula X can be prepared by bromination of the corresponding 2,6-dimethylbenzoate ester of the formula XXXII:

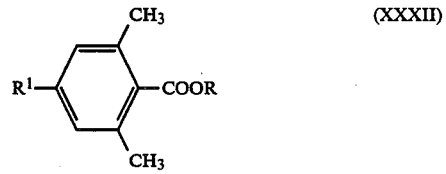

wherein R and $R^1$ are as defined previously. The bromination can be carried out using standard procedures. A convenient method involves bromination with N-bromosuccinimide or N,N-dibromo-5,5-dimethylhydantoin in refluxing carbon tetrachloride with irradiation from a sunlamp. The crude products can be recrystallized from a non-polar solvent, such as petroleum ether or cyclohexane.

The 2,6-dimethylbenzoate esters of the formula XXXI are prepared by known methods or methods analogous to known methods. See further: M. L. Bender and M. C. Chen, *Journal of the American Chemical Society*, 85, 30 (1963); ibid, 85, 37 (1963).

The compounds of the formulae I and II are acidic and they will form carboxylate salts. All such salts are within the scope of this invention, and they can be prepared by conventional methods for lipophilic carboxylic acids. For example, they can be prepared by contacting the carboxylic acid with a stoichiometric equivalent of an appropriate basic agent, in a non-aqueous or partially aqueous solvent. They can be recovered by solvent evaporation, by filtration, or by precipitation using a non-solvent followed by filtration, as appropriate. Typical salts of the compounds of formulae I and II which can be prepared include primary, secondary and tertiary amine salts, as well as alkali metal and alkaline earth metal salts. Especially favorable are sodium and potassium salts.

In a particularly convenient method of preparing salts of the compounds of formulae I and II, a solution of the compound of formula I or II in a volatile, water immiscible, organic solvent is washed with an aqueous solution containing at least a stoichiometric equivalent, and preferably a large excess, of an appropriate basic agent. After drying the organic solvent solution, it is evaporated in vacuo to give the desired salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

As indicated hereinbefore, the compounds of formulae I and II, and the salts thereof, are useful for increasing the efficiency of feed utilization in ruminant animals, i.e. animals which have multiple stomachs, one of which is a rumen. In particular, the compounds of formulae I and II are useful in cattle and sheep. For the purpose of increasing food utilization, a compound of formula I or II is administered orally to a ruminant, on a daily basis, and in an amount which is effective in increasing propionate formation in the animal's rumen. The compound of formula I or II can be administered orally by a variety of methods, in accordance with standard practices in veterinary science and animal husbandry. However, a convenient method of administering a compound of formula I or II is to blend the compound of formula I or II with the animal's food, at such a level that the animal receives an effective propionate-increasing amount.

British Pat. No. 1,197,826 describes a method for measuring the ability of compounds to increase propionate formation in the rumen of ruminant animals. The test method involves the use of an apparatus in which the digestive processes of the ruminants are conducted and studied in vitro. The animal feed, a sample of rumen contents and the compound under study are introduced into and withdrawn from a laboratory unit under carefully controlled conditions and the changes taking place are studied critically and progressively during the consumption of the feed by the microbial flora in the rumen contents. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid.

Thus, rumen fluid is collected from a fistulated cow which is fed on a commercial fattening ration plus hay. The rumen fluid is immediately filtered through cheese cloth, and 10 ml added to a 50 ml conical flask containing 400 mg of standard substrate (68% corn strach+17% cellulose+15% extracted soybean meal), 10 ml of a pH 6.8 buffer and the test compound. The flasks are gassed with oxygen free nitrogen for about 2 minutes and incubated in a shaking water bath at 39° C. for about 16 hours. All tests are conducted in triplicate. After incubation, 5 ml of the sample are mixed with 1 ml of 25% metaphosphoric acid. After 10 minutes, 0.25 ml of formic acid is added and the mixture centrifuged at 1500 r.p.m. for 10 minutes. Samples are then analyzed by gas-liquid chromatography by the method of D. W. Kellog in *J. Dairy Science,* 52, 1690 (1969). Peak heights for acetic, propionic and butyric acids are determined for samples from untreated and treated incubation flasks.

Thus, the amount of compound I or II which must be administered to a ruminant animal to increase feed utilization efficiency depends on the ability of the compound to increase propionate production in the rumen. However, a compound of formula I or II will normally be administered orally to a ruminant at a dosage in the range from 0.5 to 50 mg/kg of body weight per day.

In addition to their ability to increase feed utilization in ruminants, the compounds of formulae I and II are active as antibacterial in vitro. This makes them useful for a variety of sanitary purposes, such as sterilization of hospital surfaces, and as preservatives, e.g., paint preservatives.

The antibacterial activity of a compound of the formula I or II can be demonstrated by measuring the minimum inhibitory concentration (MIC) against a variety of organisms, according to standard procedures. Thus, the MIC's can be measured by the procedure recommended by the International Collaborative Study on Antibiotic Sensitivity Testing (Ericcson and Sherris, Acta. *Pathologica et Microbiologia Scandinav,* Supp. 217, Section B: 64–68 [1971]), which employs brain heart infusion (BHI) agar and the inocula replicating device. Overnight growth tubes are diluted 100 fold for use as the standard inoculum (20,000-10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Typical microorganisms against which the compounds of formula I and II are active in vitro are *Staphylococcus aureus, Streptococcus equi* and *Clostridium perfringens.*

The following examples and preparations are being provided for the purpose of further illustration. Infrared (IR) spectra were measured as neat liquids unless indicated otherwise, and positions of significant absorption peaks are given in reciprocal centimeters ($cm^{-1}$). Nuclear magnetic resonance (NMR) spectra were measured as solutions in deuterochloroform ($CDCl_3$) at 60 MHz, and peak positions are given in parts per million (ppm) downfield from internal tetramethylsilane. The following abbreviations for peak shapes are used: s, singlet; bs, broad singlet; d, doublet; t, triplet; q, quartet; m, multiplet. For low-resolution mass spectra (MS) and high-resolution mass spectra (HRMS), peaks are given as mass-to-charge (m/e) ratios.

EXAMPLE 1

COMPOUND I ($R^1$ is hydrogen; $R^2$ is phenyl; $R^3$ is hydrogen)

The corresponding methyl ester of the title compound (1.56 g, 0.003 mole) was dissolved in 20 ml of ethanol which contained 10 ml of 5% weight-to-volume of aqueous potassium hydroxide and heated at reflux overnight. The ethanol was removed in vacuo and the aqueous residue was extracted with two 25 ml portions of methylene chloride. The organic solvent was evaporated in vacuo to leave 1.83 g of an oil of the title compound as the potassium salt. The infrared spectrum of the potassium salt showed absorbances at 3350 and 1600 $cm^{-1}$.

The free acid of the title compound was obtained by dissolving the potassium salt in 25 ml of methylene chloride and shaking the solution with 25 ml of 1N hydrochloric acid. The methylene chloride solution was washed with 10 ml of water and dried over anhydrous magnesium sulfate. Evaporation of the filtered solution yielded 1.36 g (89% yield) of the free acid of the title compound as an amorphous foam.

NMR ($CDCl_3$): 7.8–7.1 (m, 11H), 4.8 (s, 4H) and 4.6–3.7 (m, 16H) ppm.

HRMS: m/e 508.2104 ($M^+$), 490.1969 ($M^+-H_2O$), 147.0443 (base peak).

COMPOUND I ($R^1$ is t-butyl; $R^2$ is 3,3-dimethyl-1-butenyl; $R^3$ is methyl) was prepared as its potassium salt by hydrolysis its methyl ester, in 92% yield, using the above procedure. IR(KBr): 3378, 2994, 1626, 1605 and 1580 $cm^{-1}$.

EXAMPLE 2

The compounds in Tables I, II and III were prepared by hydrolysis of the corresponding methyl or ethyl ester, using the procedure of Example 1.

TABLE I

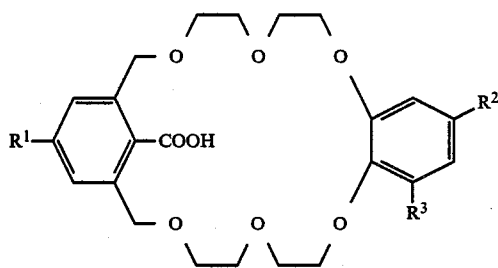

| R[1] | R[2] | R[3] | Form isolated[1] | Yield (%) | Spectral Data |
|---|---|---|---|---|---|
| H | t-butyl | H | A | 75 | IR: 3600–2500, 1720 NMR: 7.3 (s, 3H), 6.9 (m, 3H), 4.7 (s, 4H), 4.2–3.5 (m, 16H), 1.3 (s, 9H). |
| H | t-octyl | H | A | 64 | IR: 3600–2500, 1730. NMR: 7.4 (s, 3H), 7.0 (m, 3H), 4.8 (s, 4H), 4.5–3.7 (m, 16H), 1.8 (s, 2H), 1.4 (s, 6H), 0.8 (s, 9H). |
| H | cyclohexyl | H | A | 50 | IR: 2920, 1725. NMR: 7.3 (s, 3H), 6.9 (m, 3H), 4.7 (m, 4H), 4.2–3.5 (m, 16H), 2.1–1.2 (m, 13H). |
| H | t-octyl | isopropyl | K | 90 | IR[2]: 1590–1580. NMR: 7.3 (s, 3H), 6.8 (q, 2H), 4.7 (s, 4H), 4.2–3.4 (m, 16H), 1.6 (s, 2H), 1.3 (s, 6H), 1.1 (d, 6H), 0.7 (s, 9H). |
| H | t-octyl | methyl | K | 62 | IR[3]: 1625–1560, 1400. NMR 7.3 (s, 3H), 6.8 (s, 2H), 4.7 (bs, 4H), 4.2–3.5 (m, 16H), 2.3 (s, 3H), 1.6 (s, 2H), 1.3 (s, 6H), 0.8 (s, 9H). |
| H | t-octyl | thiophenoxymethyl | K | 52 | IR[2]: 3390, 2899, 1582, 1456. |
| H | n-octyl | H | A | 65 | IR: 3550–2600, 1730. NMR: 7.2 (s, 3H), 6.7 (m, 3H), 4.6 (s, 4H), 4.3–3.5 (m, 16H), 2.5 (m, 2H), 1.3–0.8 (m, 17H). HRMS: 544.3020. |
| H | n-undecyl | H | A | 45 | IR: 3600–2500, 1740. HRMS: 586.3496. |
| t-butyl | t-butyl | H | A,K | 90 | IR: 3500–2600, 1720. NMR: 7.2 (s, 2H), 6.9 (m, 3H), 4.6 (s, 4H), 4.3–3.5 (m, 16H), 1.3 (d, 18H). |
| t-butyl | t-octyl | H | A,K | 66 | IR: 1720. NMR: 7.3 (s, 2H), 6.9 (m, 3H), 4.7 (s, 4H), 4.4–3.6 (m, 16H), 1.8 (s, 2H), 1.5 (s, 15H), 0.8 (s, 9H). |
| t-butyl | n-octyl | H | A,K | 33 | IR: 2960–2850, 1735. NMR: 7.3 (s, 2H), 6.9 (m, 3H), 4.7 (bs, 4H), 4.4–3.6 (m, 16H), 1.5–0.8 (m, 24H). |
| t-butyl | n-undecyl | H | A | 62 | IR: 3300, 1700. HRMS: 642.4050. |
| t-butyl | H | methyl | A | 30 | IR: 3500–2400, 1715. NMR: 7.2 (s, 2H), 6.8 (m, 4H), 4.6 (s, 4H), 4.3–3.6 (m, 16H), 2.3 (s, 3H), 1.4 (s, 9H). |
| t-butyl | t-octyl | methyl | A,K | 62 | IR: 1720. MS: 614. |
| t-butyl | t-octyl | isopropyl | K | 90 | IR[2]: 1595–1580. |
| t-butyl | t-butyl | isopropyl | K | 70 | IR[2]: 1600–1580. |
| t-butyl | t-butyl | t-butyl | K | 42 | IR[2]: 1600–1585. |
| t-butyl | t-octyl | benzyl | K | 58 | IR[2]: 1600–1580. |
| t-butyl | 4-t-butyl-phenyl | H | A | 75 | IR[2]: 1720. |
| t-butyl | 4-t-butyl-phenyl | t-butyl | K | 80 | IR[2]: 1600–1585. |
| t-butyl | t-octyl | methoxymethyl | K | 90 | IR[2]: 1621. NMR: 7.3 (s, 2H), 6.8 (m, 2H), 4.4 (m, 6H), 4.2–3.2 (m, 19H), 1.6 (s, 2H), 1.3 (s, 15H), 0.7 (s, 9H). |
| t-butyl | methyl | t-octyl | K | 60 | IR[3]: 1610. |
| t-butyl | t-butyl | t-octyl | K | 48 | IR[2]: 1600. |

TABLE I-continued

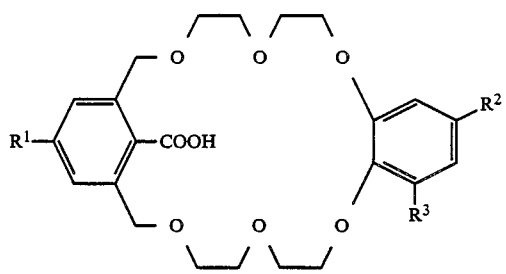

| R¹ | R² | R³ | Form isolated[1] | Yield (%) | Spectral Data |
|---|---|---|---|---|---|
| t-butyl | t-octyl | hydroxymethyl | K | 95 | IR[2]: 3289, 3067, 1600. |
| t-butyl | 1-adamantyl | methyl | A,K | 58 | IR: 1715. NMR: 7.2 (s, 2H), 6.8 (s, 2H), 4.6 (s, 4H), 4.4–3.5 (m, 16H), 2.3 (s, 3H), 2.0 (s, 9H), 1.8 (s, 6H), 1.3 (s, 9H). |
| t-butyl | 3,3-dimethylbutanoyl | methyl | K | 63 | IR[2]: 3425, 2933, 1672, 1587. |
| t-butyl | 3,3-dimethylbutyl | methyl | K | 68 | IR[2]: 1590. |
| t-butyl | t-octyl | benzyloxymethyl | K | 65 | IR[2]: 1600. |
| t-butyl | t-octyl | 2-methylbenzyloxymethyl | K | 61 | IR[2]: 1590. |
| t-butyl | t-octyl | 4-methylbenzyloxymethyl | K | 47 | IR[2]: 3448, 2915, 1595. |
| t-butyl | t-octyl | 2-phenylethyl | K | 66 | IR[2]: 3425, 2941, 1587. |
| t-butyl | t-octyl | 2-(4-tolyl)ethyl | K | 67 | IR[2]: 3390, 2907, 1580. |
| t-butyl | t-octyl | 3-phenylpropyl | K | 62 | IR[2]: 3390, 2915, 1580. |
| t-butyl | t-octyl | phenoxymethyl | A,K | 54 | NMR: 7.3–6.8 (m, 9H), 5.1 (s, 2H), 4.6 (s, 4H), 4.4–3.5 (m, 16H), 1.7 (s, 2H), 1.4 (s, 15H), 0.8 (s, 9H). |
| t-butyl | t-octyl | 2-(2-fluorophenyl)ethyl | K | 83 | IR[2]: 3390, 2907, 1580. |
| t-butyl | t-octyl | 2-(2-tolyl)ethyl | K | 68 | IR[2]: 3367, 2899, 1580. |
| t-butyl | t-octyl | 4-methylthiophenoxymethyl | K | 61 | IR[2]: 3367, 2882, 1580. |
| H | t-octyl | 2-(3-tolyl)ethyl | K | 70 | IR[2]: 3401, 2941, 1587. |
| H | t-octyl | 2-(t-butylphenyl)ethyl | K | 72 | IR[2]: 3484, 2976, 1590. |
| t-butyl | t-octyl | thiophenoxymethyl | K | 78 | IR[2]: 3425, 2967, 1582. |

[1] In this column, the entry "A" indicates that the compound was isolated as the free acid, and the entry K indicates that it was isolated as the potassium salt.
[2] IR taken as a KBr disk.
[3] IR taken as a CH₂Cl₂ solution.

TABLE II

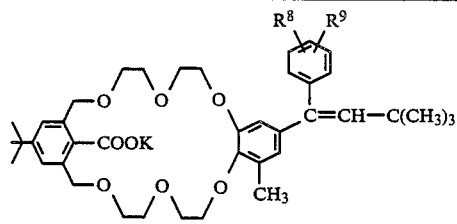

| R⁸ and R⁹ | Yield (%) | Spectral Data |
|---|---|---|
| H; H | 71 | IR (KBr): 3390, 2924, 1577 |
| 4-methylthio; H | 63 | IR (KBr): 3460, 2994, 6100. |
| 2-methyl; H | 56 | IR (KBr): 3425, 2967, 1605, 1580. |
| 3-methoxy; H | 56 | IR (KBr): 3460, 3003, 1587. |
| 4-methoxy; H | 48 | IR (CHCl₃): 1600. |
| 2,6-dimethyl | 59 | IR (KBr): 3390, 2941, 1575. |
| 2,6-dimethoxy | 69 | IR (CH₂Cl₂): 1590. |
| 2-ethyl; H | 47 | IR (KBr): 3378, 2915, 1603, 1577. |
| 2-methoxy; H | 63 | IR (KBr): 3401, 2924, 1582. |

TABLE II-continued

| R⁸ and R⁹ | Yield (%) | Spectral Data |
|---|---|---|
| 2-methylthio | 58 | IR (KBr): 3401, 2924, 1577. |
| 3,5-dimethyl | 71 | IR (KBr): 3401, 2941, 1629, 1600. |
| 3-methyl; H | 46 | IR (KBr): 3378, 2907, 1575. |
| 4-methyl; H | 61 | IR (KBr): 3367, 2899, 1572. |

TABLE III

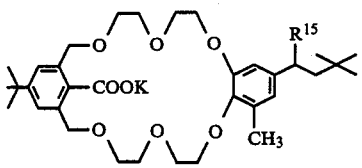

| R[15] | Yield (%) | Spectral Data |
|---|---|---|
| n-butyl | 90 | IR (KBr): 3401, 2907, 1613, 1595. NMR[1]: 7.2 (s, 2H), 6.5 (s, 2H), 4.6 (s, 4H), 4.3–3.5 (m, 16H), 2.4 (m, 1H), 2.2 (s, 3H), 1.6–0.7 (m, 29H). |
| n-hexyl | 36 | IR (CHCl$_3$): 1601. |
| phenyl | 73 | IR (KBr): 3390, 2924, 1605. |
| n-octyl | 65 | IR (CHCl$_3$): 1600. |
| isoamyl | 75 | IR (CHCl$_3$): 1580. |
| ethyl | 51 | IR (CHCl$_3$): 1595. |
| 4-tolyl | 60 | IR (CHCl$_3$): 1580. |
| 2-tolyl | 38 | IR (CHCl$_3$): 1590. |
| 3-methoxyphenyl | 21 | IR(CHCl$_3$): 1575. |
| 4-methylthiophenyl | 76 | IR (KBr): 3413, 2967, 1587. |
| 4-methoxyphenyl | 53 | IR (CHCl$_3$): 1590. |

[1]Measured as the free acid.

EXAMPLE 3

COMPOUND I ($R^1$ is t-butyl; $R^2$ is t-octyl; $R^3$ is 2-pyridylthiomethyl)

The title compound of Preparation Q (0.8 g, 0.0011 mole) was hydrolyzed by heating in ethanol (60 ml) and 15 ml of 10% weight-to-volume of aqueous potassium hydroxide for 18 hours at 100° C. The ethanol was removed in vacuo and the work-up of Example 1 was employed to yield the potassium salt of the title carboxylic acid (0.5 g, 60% yield).

IR (KBr): 3390 and 1575 cm$^{-1}$.

The corresponding free acid was obtained by dissolving the potassium salt in 15 ml methylene chloride and shaking the solution with 15 ml 1N hydrochloric acid. The methylene chloride solution was worked up as in Example 1 to give the acid (0.4 g, 84% yield).

NMR (CDCl$_3$): 8.4 (d, 1H), 7.4–6.6 (m, 7H), 4.6 (s, 4H), 4.4 (s, 2H), 4.4–3.5 (m, 16H), 1.6 (s, 2H), 1.3 (s, 15H), and 0.6 (s, 9H), ppm.

Also prepared by this method were the following compounds:

TABLE IV

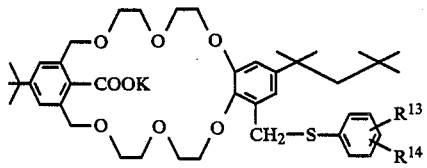

| R[13] and R[14] | Yield (%) | Spectral Data |
|---|---|---|
| 2-methoxy; H | 57 | IR (KBr): 3390, 2429, 1580. |
| 2-methyl; H | 66 | IR (KBr): 3390, 2915, 1585. |
| 3-methoxy; H | 63 | IR (KBr): 3390, 2924, 1587. |
| 4-methoxy; H | 71 | IR (KBr): 3390, 2907, 1587. |
| 2-bromo; H | 62 | IR (KBr): 3367, 2907, 1580. |
| 4-bromo; H | 73 | IR (KBr): 3413, 2915, 1587. |
| 4-fluoro; H | 73 | IR (KBr): 3390, 2915, 1582. |
| 2-chloro; H | 41 | NMR[1]: 7.2 (m, 6H), 6.8 (s, 2H), 4.6 (s, 4H), 4.3–3.5 (m, 18H), 1.7 (s, 2H), 1.3 (d, 15H), 0.7 (s, 9H). |
| 3-chloro; H | 97 | IR (CH$_2$Cl$_2$): 1590. |
| 4-t-butyl; H | 75 | IR (CH$_2$Cl$_2$): 1600. |

TABLE IV-continued

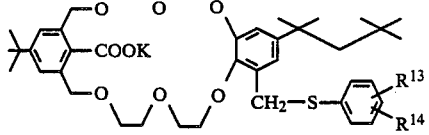

| R[13] and R[14] | Yield (%) | Spectral Data |
|---|---|---|
| 2,6-dichloro | 66 | IR (KBr): 3390, 2994, 1585. |
| 2,6-dimethyl | 61 | IR (KBr): 3448, 2959, 1592. |
| 2-ethyl; H | 82 | IR (KBr): 3390, 2915, 1585. |
| 2,3-dimethyl | 79 | IR (KBr): 3367, 2915, 1580. |

EXAMPLE 4

COMPOUND II ($R^1$ is t-butyl; $R^4$ is hydrogen; $R^5$ and $R^6$ form a cyclohexylidene ring)

The title ester of Preparation T (4.5 g, 7.9 mole) was dissolved in 200 ml ethanol and treated at 100° C. with 100 ml of a solution of 15% weight-to-volume of potassium hydroxide in water. The title compound (2.7 g, 57% yield) was isolated as a foam using the working procedure employed in Example 1 to obtain the potassium salt.

IR: 3378 and 1587 cm$^{-1}$.

The products in Table V were obtained from the corresponding ester using the above procedure.

TABLE V

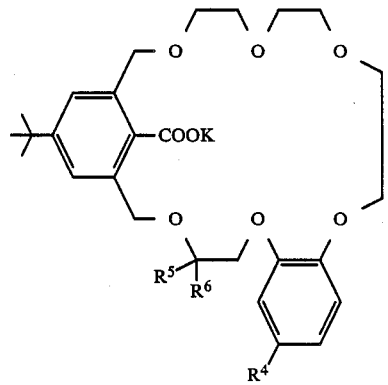

| R[4] | R[5] and R[6]; or R[5]R[6]C = | Yield (%) | Spectral Data |
|---|---|---|---|
| H | 4-t-butylcyclohexylidene | 39 | IR (KBr): 3356, 2899, 1721, 1600. |
| H | 4-chlorophenoxymethyl; H | 85 | IR (KBr): 3328, 2900, 1590. |
| H | 3,3,5-trimethylcyclohexylidene | 47 | IR (KBr): 3367, 2899, 1587. |
| H | 4-t-butylphenoxymethyl; H | 75 | IR (KBr): 3378, 2915, 1605. |
| H | phenoxymethyl; H | 75 | IR (KBr): 3367, 2907, 1595. |
| H | thiophenoxymethyl; H | 83 | IR (KBr): 3413, 2959, 1587. |
| t-octyl | cyclohexylidene | 66 | IR (CHCl$_3$): 1595. |
| t-octyl | hexyl; H | 56 | IR (CHCl$_3$): 1590 |
| t-octyl | 3,3,5-trimethylcyclohexylidene | 72 | IR (KBr): 3367, 2899, 1590. |
| t-octyl | cycloheptylidene | 36 | IR (KBr): 3390, 2899, 1582. |
| t-octyl | phenoxymethyl; H | 45 | IR (KBr): 3367, 2899, 1595. |
| t-octyl | thiophenoxymethyl; H | 67 | IR (KBr): 3367, 2890, 1575. |

EXAMPLE 5

The compounds in Tables VI, VII and VIII can be prepared by reaction of the appropriate diol of formula XI or XII with methyl 2,6-di(bromomethyl)-4-t-butylbenzoate and sodium hydride according to the procedure of Preparation J, followed by hydrolysis of the macrocyclic ester thus obtained according to Example 1.

TABLE VI

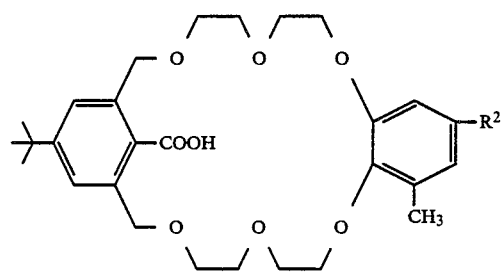

| $R^2$ |
|---|
| methyl |
| dodecyl |
| cyclopentyl |
| cyclooctyl |
| 2-tolyl |
| 4-butylphenyl |
| 1,3,3-trimethyl-1-butenyl |
| 3,3-dimethyl-1-n-butyl-1-butenyl |
| 3,3-dimethyl-1-(4-propylphenyl)-1-butenyl |
| 3,3-dimethyl-1-(3-isopropoxyphenyl)-1-butenyl |
| 3,3-dimethyl-1-(4-propylthiophenyl)-1-butenyl |
| 3,3-dimethyl-1-(2-naphthyl)-1-butenyl |
| 3,3-dimethyl-1-n-butylbutyl |
| 3,3-dimethyl-1-(4-propylphenyl)butyl |
| 3,3-dimethyl-1-(3-isopropoxyphenyl)butyl |
| 3,3-dimethyl-1-(4-propylthiophenyl)butyl |
| 3,3-dimethyl-1-(2-naphthyl)butyl |

TABLE VII

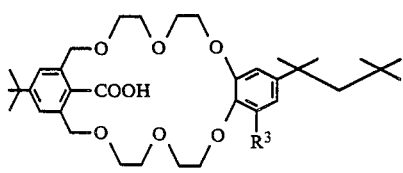

| $R^3$ |
|---|
| 3-fluorobenzyl |
| 4-chlorobenzyl |
| 4-phenylbutyl |
| 3-n-propylbenzyloxymethyl |
| 4-isopropoxybenzyloxymethyl |
| 4-n-propylthiobenzyloxymethyl |
| 3-(n-propyl)thiophenoxymethyl |
| 4-(isopropoxy)thiophenoxymethyl |
| 4-(n-propylthio)thiophenoxymethyl |
| 3,4-dichlorothiophenoxymethyl |

TABLE VIII

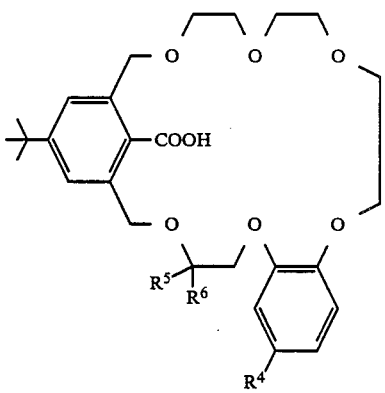

| $R^4$ | $R^5$ and $R^6$; or $R^5R^6C =$ |
|---|---|
| t-octyl | H; H |
| t-octyl | $CH_3$; H |
| $CH_3$ | n-octyl; H |
| isopropyl | cyclopentylidene |
| n-hexyl | cycloheptylidene |
| H | t-octyl; H |

EXAMPLE 6

5-(3,3-Dimethylbutanoyl)-3-methyl-1,2-di(2-[2-hydroxyethoxy]ethoxy)benzene

The title compound from Preparation I (5 g, 0.0088 mole) was dissolved in methanol (50 ml) and 4 ml of 1N hydrochloric acid were added. The resulting solution was stirred for 1 hour at 25° C. and the methanol was removed by evaporation in vacuo, and the aqueous residue extracted with 100 ml methylene chloride. The organic solution extract was washed with 50 ml saturated aqueous sodium bicarbonate and 25 ml brine. After drying over anhydrous magnesium sulfate, the solution was evaporated in vacuo to an oil of the title compound (3.3 g, 94% yield).

NMR (CDCl$_3$): 7.4 (s, 2H), 4.2 (m, 4H), 3.8 (m, 12H), 3.2 (s, 2H), 2.8 (s, 2H), 2.3 (s, 3H) and 1.1 (s, 9H) ppm.
IR: 3375 and 1660 cm$^{-1}$.

Hydrolysis of the appropriate bis(tetrahydropyranyl)protected diol, according to the above procedure, afforded the compounds in Tables IX and X.

TABLE IX

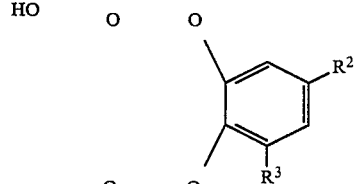

| $R^2$ | $R^3$ | Spectral Data |
|---|---|---|
| H | H | IR: 3350, 1600, 1500, 1250. NMR: 6.9 (s, 4H), 4.2–3.6 (m, 18H). |
| t-butyl | H | IR: 3400, 2950, 2860, 1525. NMR: 6.7 (m, 3H), 4.0–3.4 (m, 16H), 3.3 (s, 2H), 1.05 (s, 9H). |
| phenyl | H | IR: 3350, 1600, 1510, 1490. |

TABLE IX-continued

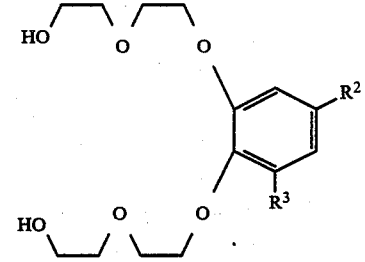

| R² | R³ | Spectral Data |
|---|---|---|
| t-octyl | H | NMR: 7.6–7.0 (m, 8H), 4.4–3.6 (m, 18H). IR: 3600, NMR: 7.0 (m, 3H), 4.3–4.0 (m, 4H), 3.9–3.5 (m, 14H), 1.7 (s, 2H), 1.4 (s, 6H), 0.9 (s, 9H). |
| t-octyl | isopropyl | IR: 3450, 2975, 1575. NMR: 6.8 (q, 2H), 4.3–4.0 (m, 4H), 4.0–3.6 (m, 18H), 1.7 (s, 2H), 1.4 (s, 6H), 1.2 (d, 6H), 0.7 (s, 9H). |
| t-octyl | methyl | IR: 3600. NMR: 6.8 (s, 2H), 4.3–4.0 (m, 4H), 4.0–3.5 (m, 14H), 2.4 (s, 3H), 1.8 (s, 2H), 1.4 (s, 6H), 0.8 (s, 9H). |
| t-butyl | morpholino-methyl | IR: 3600. NMR: 6.8 (q, 2H), 4.2–4.0 (m, 4H), 4.0–3.3 (m, 18H), 2.5 (m, 4H), 1.3 (s, 9H). |
| t-octyl | thiophenoxy-methyl | IR: 3600. NMR: 7.2 (m, 5H), 6.7 (q, 2H), 4.3–3.5 (m, 20H), 1.6 (s, 2H), 1.2 (s, 6H), 0.8 (s, 9H). |
| H | methyl | IR: 3400, 2940, 2860. |
| t-butyl | isopropyl | IR: 3600–3400. NMR: 6.8 (q, 2H), 4.2–3.5 (m, 18H), 1.2 (s, and d, 15H). |
| t-butyl | t-butyl | NMR: 6.9 (q, 2H), 4.3–3.4 (m, 18H), 1.3 (d, 18H). |
| t-octyl | benzyl | NMR: 7.2 (m, 5H), 6.8 (m, 2H), 4.3–3.6 (m, 18H), 1.8 (s, 2H), 1.4 (s, 6H), 0.8 (s, 9H). |
| 4-t-butyl-phenyl | H | NMR: 7.5 (s, 4H), 7.2 (m, 3H), 4.4–3.6 (m, 16H), 3.1 (s, 2H), 1.4 (s, 9H). |
| 4-t-butyl-phenyl | t-butyl | NMR: 7.4 (s, 4H), 7.2–6.9 (m, 2H), 4.3–3.5 (m, 16H), 3.0 (s, 2H), 1.4 (s, 9H), 1.3 (s, 9H). |
| methyl | methyl | NMR: 6.9 (s, 2H), 4.3–3.4 (m, 16H), 2.3 (s, 6H), 1.7 (s, 2H). |
| t-octyl | morpholino-methyl | IR: 3400, 2950–2840, 1600. NMR: 7.0 (q, 2H), 4.3–3.5 (m, 20H), 3.0 (s, 2H), 2.5 (m, 4H), 1.7 (s, 2H), 1.4 (s, 6H), 0.8 (s, 9H). |
| methyl | t-octyl | NMR: 6.8–7.0 (dd, 2H), 4.4–3.4 (m, 18H), 2.4 (s, 3H), 2.0 (s, 2H), 1.6 (s, 6H), 0.9 (s, 9H). |
| 1-adamantyl | methyl | IR: 3400. NMR: 6.9 (s, 2H), 4.4–3.5 (m, 16H), 3.2 (s, 2H), 2.2 (s, 3H), 2.0 (bs, 9H), 1.8 (bs, 6H). |
| 3,3-dimethyl-butyl | methyl | IR: 3400, 1600. NMR: 6.7 (m, 2H), 4.3–3.5 (m, 16H), 2.2 (s, 3H), 1.5 (m, 4H), 1.0 (s, 9H). |
| t-octyl | 2-phenyl-ethyl | NMR: 7.2 (s, 5H), 6.7 (q, 2H), 4.2–3.5 (m, 18H), 2.9 (s, 4H), 1.7 (s, 2H), 1.4 (s, 6H), 0.7 (s, 9H). |
| t-octyl | 2-(4-tolyl)-ethyl | NMR: 7.0 (s, 4H), 6.8 (m, 2H), 4.3–3.5 (m, 16H), 3.3 (s, 2H), 2.9 (s, 4H), 2.4 (s, 3H), 1.7 (s, 2H), 1.4 (s, 6H), 0.8 (s, 9H). |
| t-octyl | 3-phenyl-propyl | NMR: 7.2 (s, 5H), 6.8 (m, 2H), 4.2–3.4 (m, 16H), 3.3 (s, 2H), 2.6 (m, 4H), 1.9 (m, 2H), 1.7 (s, 2H), 1.4 (s, 6H), 0.8 (s, 9H). |
| t-octyl | 2-(2-fluoro-phenyl)ethyl | NMR: 7.1 (m, 4H), 6.7 (m, 2H), 4.3–3.6 (m, 16H), 3.2 (s, 2H), 2.9 (s, 4H), 1.7 (s, 2H), 1.4 (s, 6H), 0.8 (s, 9H). |
| t-octyl | 2-(2-tolyl)-ethyl | NMR: 7.1 (s, 4H), 6.7 (m, 4H), 4.3–3.5 (m, 16H), 3.2 (s, 2H), 2.9 (s, 4H), 2.4 (s, 3H), 1.7 (s, 2H), 1.4 (s, 6H), 0.8 (s, 9H). |
| t-octyl | 2-(3-tolyl)-ethyl | NMR: 7.2–6.6 (m, 6H), 4.2–3.4 (m, 16H), 3.3 (d, 2H), 2.8 (s, 4H), 2.3 (s, 3H), 1.0 (s, 2H), 1.3 (s, 6H), 0.7 (s, 9H). |
| t-octyl | 2-(4-t-butyl-phenyl)ethyl | NMR: 7.3 (m, 4H), 6.8 (q, 2H), 4.3–3.6 (m, 16H), 3.4 (s, 2H), 3.0 (s, 4H), 1.8 (s, 2H), 1.4 (s, 15H), 0.8 (s, 9H). |

TABLE X

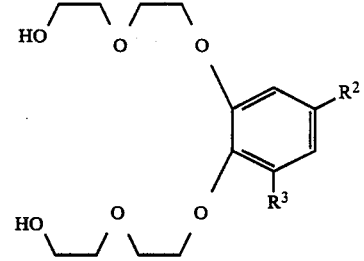

| R¹³ and R¹⁴ | Spectral Data |
|---|---|
| 2-methoxy; H | NMR: 7.3–6.7 (m, 6H), 4.3–3.3 (m, 23H), 1.6 (s, 2H), 1.4 (s, 6H), 0.8 (s, 9H). |
| 3-methyl; H | NMR: 7.1 (m, 4H), 6.8 (m, 2H), 4.3–3.6 (m, 18H), 3.3 (s, 2H), 2.4 (s, 3H), 1.7 (s, 2H), 1.4 (s, 6H), 0.8 (s, 9H). |
| 3-methoxy; H | NMR: 7.4–6.8 (m, 6H), 4.4–3.4 (m, 23H), 1.7 (s, 2H), 1.4 (s, 6H), 0.8 (s, 9H). |
| 4-methoxy; H | NMR: 7.4 (m, 2H), 6.8 (m, 4H), 4.3–3.5 (m, 21H), 3.2 (s, 2H), 1.6 (s, 2H), 1.2 (s, 6H), 0.7 (s, 9H). |
| 2-bromo; H | NMR: 7.5–6.8 (m, 6H), 4.3–3.5 (m, 18H), 3.0 (s, 2H), 1.6 (s, 2H), 1.2 (s, 6H), 0.7 (s, 9H). |
| 4-bromo; H | NMR: 7.2 (m, 4H), 6.7 (m, 2H), 4.3–3.5 (m, 18H), 3.3 (m, 2H), 1.6 (s, 2H), 1.3 (s, 6H), 0.7 (s, 9H). |
| 4-fluoro; H | NMR: 7.4–6.7 (m, 6H), 4.2–3.5 (m, 18H), 3.2 (m, 2H), 1.6 (s, 2H), 1.2 (s, 6H), 0.7 (s, 9H). |

TABLE X-continued

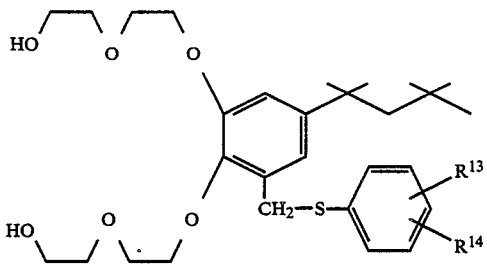

| $R^{13}$ and $R^{14}$ | Spectral Data |
|---|---|
| 2-chloro; H | IR: 3425, 2950, 2860, 1580. NMR: 7.2 (m, 4H), 6.8 (s, 2H), 4.4–3.5 (m, 18H), 3.1 (s, 2H), 1.6 (s, 2H), 1.3 (s, 6H), 0.7 (s, 9H). |
| 3-chloro; H | NMR: 7.2–6.8 (m, 6H), 4.4–3.5 (m, 18H), 3.3 (s, 2H), 1.6 (s, 2H), 1.3 (s, 6H), 0.7 (s, 9H). |
| 4-t-butyl; H | NMR: 7.3 (s, 4H), 6.8 (s, 2H), 4.3–3.5 (m, 18H), 3.3 (s, 2H), 1.6 (s, 2H), 1.3 (d, 15H), 0.8 (s, 9H). |
| 2,6-dichloro | NMR: 7.3 (m, 3H), 6.8 (m, 1H), 6.5 (m, 1H), 4.4–3.6 (m, 18H), 3.1 (s, 2H), 1.6 (s, 2H), 1.4 (s, 6H), 0.8 (s, 9H). |

EXAMPLE 7

The compounds in Table XI can be prepared by reaction of the appropriate catechol with 2-(2-[2-chloroethoxy]ethoxy)tetrahydropyran according to Preparation I, followed by hydrolysis according to the procedure of Example 6.

TABLE XI

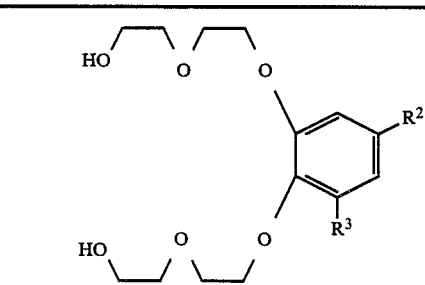

| $R^2$ | $R^3$ |
|---|---|
| methyl | methyl |
| dodecyl | ethyl |
| cyclopentyl | isopropyl |
| cyclooctyl | hydrogen |
| n-butylphenyl | methyl |
| t-octyl | 3-fluorobenzyl |
| t-octyl | 4-chlorobenzyl |
| t-octyl | 4-phenylbutyl |
| t-octyl | 3-n-propylbenzyloxymethyl |
| t-octyl | 4-isopropoxybenzyloxymethyl |
| t-octyl | 4-n-propylthiobenzyloxymethyl |
| t-octyl | 3-(n-propyl)thiophenoxymethyl |
| t-octyl | 4-(isopropoxy)thiophenoxymethyl |
| t-octyl | 4-(n-propylthio)thiophenoxymethyl |
| t-octyl | 3,4-dichlorothiophenoxymethyl |

EXAMPLE 8

5-(1-Phenyl-3,3-dimethyl-1-butenyl)-3-methyl-1,2-di(2-[2-hydroxyethoxy]ethoxy)benzene The bis(tetrahydropyran)protected diol of Preparation I (5.9 g, 0.01 mole) was dissolved in 100 ml of diethyl ether and stirred under a nitrogen atmosphere at 25° C. while phenylmagnesium chloride (8.7 ml of a commercial 2.4M solution in tetrahydrofuran, 0.02 moles) was added dropwise over 0.5 hour. The reaction mixture was stirred at 25° C. overnight. A saturated aqueous ammonium chloride solution (15 ml) was added dropwise at 10° C. to give a precipitate and a clear solution. The solution was filtered, dried over anhydrous magnesium sulfate and evaporated to a colorless oil (6.2 g).

An aliquot (3.0 g, 0.005 mole) of the above oil was dissolved in 100 ml of tetrahydrofuran and 25 ml of methanol containing 25 ml of 1N hydrochloric acid and stirred at 25° C. for 2 hours. The organic solvents were evaporated in vacuo and the aqueous residue was extracted with two 50 ml portions of diethyl ether. The ether extracts were combined and washed with 20 ml water and 20 ml brine and dried over anhydrous magnesium sulfate. Solvent evaporation in vacuo gave the title compound as a colorless oil (2.28 g, 95% yield).

IR: 3400 cm$^{-1}$.

NMR (CDCl$_3$): 7.3 (m, 5H), 6.6 (m, 2H), 6.0 (s, 1H), 4.2–3.5 (m, 16H), 2.2 (d, 3H) and 1.0 (s, 9H). The doubling of the catechol's 3-methyl group at 2.2 ppm indicated that both E and Z isomers were present.

Following the above procedure, but using the appropriate Grignard reagent, the compounds in Table XII were prepared.

TABLE XII

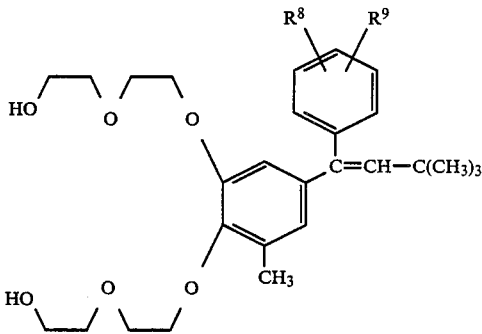

| $R^8$ and $R^9$ | Spectral Data |
|---|---|
| 4-methylthio; H | NMR: 7.2 (m, 4H), 6.6 (s, 2H), 6.0 (s, 1H), 4.3–3.5 (m, 18H), 2.4 (s, 3H), 2.2 (d, 3H), 1.0 (s, 9H). |
| 2-methyl; H | NMR: 7.2 (s, 4H), 6.6 (m, 2H), 6.0 (s, 1H), 4.2–3.5 (m, 16H), 3.2 (bs, 2H), 2.2 (s, 3H), 2.1 (s, 3H), 1.0 (s, 9H). |
| 3-methoxy; H | IR: 3375, 1600. NMR: 7.4–6.6 (m, 6H), 6.0 (s, 1H), 4.3–3.5 (m, 19H), 3.2 (s, 2H), 2.2 (s, 3H), 1.0 (s, 9H). |
| 4-methoxy; H | NMR: 7.3–6.5 (m, 6H), 5.9 (s, 1H), 4.3–3.5 (m, 19H), 3.2 (s, 2H), 2.2 (s, 3H), 1.0 (s, 9H). |
| 2,6-dimethyl | NMR: 7.0 (m, 3H), 6.6 (m, 2H), 6.0 (d, 1H), 4.2–3.3 (m, 18H), 2.3 (bs, 9H), 0.9 (s, 9H). |
| 2,6-dimethoxy | NMR: 7.2 (m, 1H), 6.5 (m, 4H), 6.0 (s, 1H), 4.2–3.6 (m, 22H), 3.0 (s, 2H), 2.2 (s, 3H), 0.9 (s, 9H). |
| 2-ethyl; H | NMR: 7.1 (m, 14H), 6.6 (m, 2H), 6.1 (s, 1H), 4.2–3.4 (m, 16H), 3.2 (s, 2H), 2.4 (m, 2H), 2.2 (s, 3H), 1.0 (m, 12H). |
| 2-methoxy; H | NMR: 7.3–6.4 (m, 6H), 5.9 (m, 1H), 4.2–3.2 (m, 21H), 2.1 (s, 3H), 0.9 (s, 9H). |
| 2-methylthio; H | NMR: 7.2 (m, 4H), 6.6 (m, 2H), 6.0 (s, 1H), 4.2–3.4 (m, 16H), 3.3 (bs, 2H), 2.4 (s, 3H), 2.2 (s, 3H), 1.0 (s, 9H). |

TABLE XII-continued

[Structure: benzene ring with HO-CH2CH2-O-CH2CH2-O- and HO-CH2CH2-O-CH2CH2-O- substituents, CH3, and C=CH—C(CH3)3 group with R8, R9 on attached phenyl]

| R8 and R9 | Spectral Data |
|---|---|
| 3,5-dimethyl | NMR: 6.8 (m, 3H), 6.6 (m, 2H), 6.0 (d, 1H), 4.3–3.4 (m, 18H), 2.3 (m, 9H), 1.0 (s, 9H). |
| 3-methyl; H | NMR: 7.0 (m, 4H), 6.5 (m, 2H), 6.0 (d, 1H), 4.2–3.4 (m, 18H), 2.2 (m, 6H), 1.0 (s, 9H). |
| 4-methyl; H | NMR: 7.0 (m, 4H), 6.6 (m, 2H), 6.0 (s, 1H), 4.2–3.4 (m, 16H), 2.2 (d, 6H), 1.6 (bs, 2H), 1.0 (s, 9H). |

EXAMPLE 9

5-(1-Phenyl-3,3-dimethylbutyl)-3-methyl-1,2-di(2-[2-hydroxyethoxy]ethoxy)benzene 5-(1-Hydroxy-1-phenyl-3,3-dimethyl-1-butyl)-3-methyl-1,2-di(2-[2-(2-tetrahydropyranyloxy)ethoxy]ethoxy)benzene (3.0 g, 0.005 mole) was dissolved in absolute ethanol (100 ml) with 10% Pd/C catalyst (0.4 g). This mixture was shaken in a Parr hydrogenator at 50 psi hydrogen pressure for 18 hours. The solution was filtered and 1N HCl (10 ml) was added to the filtrate. After 2 hours, the alcohol was evaporated in vacuo, the residual oil was dissolved in methylene chloride (50 ml) and washed with water (25 ml), brine (25 ml) and dried over MgSO4. Evaporation gave the title compound as a colorless oil (2.17 g, 95% yield).

IR: 3400, 1600.
NMR (CDCl3): 7.2 (m, 5H), 6.7 (m, 2H), 4.2–3.6 (m, 18H), 2.1 (m, 6H), 0.9 (s, 9H).

EXAMPLE 10

Reaction of 5-(3,3-dimethylbutanoyl)-3-methyl-1,2-di(2-[2-(2-tetrahydropyranoyloxy)ethoxy]ethoxy)benzene with the appropriate Grignard reagent of the formula $R^{15}MgX$ (wherein X is Cl or Br) according to the procedure of Example 8, followed by hydrogenation and hydrolysis according to the procedure of Example 9, afforded the compounds in Table XIII.

TABLE XIII

[Structure with $R^{15}$]

| $R^{15}$ | Spectral Data |
|---|---|
| n-butyl | NMR: 6.5 (s, 2H), 4.3–3.6 (m, 16H), 3.4 (s, 2H), 2.5 (m, 1H), 2.3 (s, 3H), 1.7–0.8 (m, 20H). |
| n-hexyl | NMR: 6.6 (m, 2H), 4.4–3.6 (m, 16H), 3.4 (s, 2H), 2.4 (m, 1H), 2.3 (s, 3H), |

TABLE XIII-continued

[Structure with $R^{15}$]

| $R^{15}$ | Spectral Data |
|---|---|
| | 1.6–0.7 (m, 25H). |
| n-octyl | NMR: 6.6 (m, 2H), 4.3–3.6 (m, 16H), 3.3 (s, 2H), 2.3 (m, 4H), 1.7–0.7 (m, 27H). |
| isoamyl | NMR: 6.7 (m, 2H), 4.3–3.6 (m, 18H), 2.3 (m, 4H), 1.9–0.7 (m, 22H). |
| ethyl | NMR: 6.6 (m, 2H), 4.3–3.5 (m, 18H), 2.3 (m, 4H), 1.5 (m, 4H), 0.9 (m, 12H). |
| 4-tolyl | NMR: 7.1 (m, 4H), 6.7 (m, 2H), 4.3–3.5 (m, 16H), 3.2 (s, 2H), 2.3 (m, 9H), 0.8 (s, 9H). |
| 2-tolyl | NMR: 7.1 (m, 4H), 6.7 (m, 2H), 4.3–3.5 (m, 16H), 3.2 (s, 2H), 2.3 (m, 9H), 0.9 (m, 9H). |
| 3-methoxyphenyl | NMR: 7.2–6.6 (m, 6H), 4.2–3.2 (m, 21H), 2.0 (m, 6H), 0.8 (s, 9H). |
| 4-methylthiophenyl | NMR: 7.1 (m, 4H), 6.5 (m, 2H), 4.2–3.4 (m, 16H), 3.2 (s, 2H), 2.4 (s, 3H), 2.2 (s, 3H), 2.0 (m, 3H), 0.9 (d, 9H). |
| 4-methoxyphenyl | NMR: 7.0–6.6 (m, 6H), 4.2–3.4 (m, 21H), 2.2–1.8 (m, 6H), 0.8 (s, 9H). |

EXAMPLE 11

The compounds in Table XIV can be prepared from 5-(3,3-dimethylbutanoyl)-3-methyl-1,2-di(2-[2-(2-tetrahydropyranyloxy)ethoxy]ethoxy)benzene by reaction with the appropriate Grignard reagent followed by hydrolysis according to the procedure of Example 8, or by reaction with the appropriate Grignard reagent according to the procedure of Example 8 followed by hydrogenation according to the procedure of Example 9.

TABLE XIV

[Structure with $R^2$]

| $R^2$ |
|---|
| 1,3,3-trimethyl-1-butenyl |
| 3,3-dimethyl-1-n-butyl-1-butenyl |
| 3,3-dimethyl-1-(4-propylphenyl)-1-butenyl |
| 3,3-dimethyl-1-(3-propoxyphenyl)-1-butenyl |
| 3,3-dimethyl-1-(4-propylthiophenyl)-1-butenyl |
| 3,3-dimethyl-1-(2-naphthyl)-1-butenyl |
| 3,3-dimethyl-1-n-butylbutyl |
| 3,3-dimethyl-1-(4-propylphenyl)butyl |
| 3,3-dimethyl-1-(3-isopropoxyphenyl)butyl |
| 3,3-dimethyl-1-(4-propylthiophenyl)butyl |
| 3,3-dimethyl-1-(2-naphthyl)butyl |

EXAMPLE 12

1-([1-Hydroxycyclohexyl]methoxy)-2-(2-[2-hydroxyethoxy]ethoxy)ethoxy)benzene

A mixture of the product of Preparation S (3 g, 0.0124 mole) and the epoxide of methylenecyclohexane (1.4 g, 0.0124 mole, J. Amer. Chem. Soc., 87, 1353 (1965)) and potassium carbonate (1.7 g, 0.012 mole) were combined without solvent and heated to 120° C. with stirring under a nitrogen atmosphere for 20 hrs. The reaction mixture was cooled to 25° C., 25 ml diethyl ether were added and the ethereal solution was washed with 10 ml 10% weight-to-volume of potassium hydroxide in water, 10 ml water and 10 ml brine. The washed etheral solution were dried over anhydrous magnesium sulfate and evaporated in vacuo to a brown oil (4.17 g, (95% yield) which was used without further purification.

NMR (CDCl$_3$): 6.8 (s, 4H), 4.1 (m, 2H), 3.9–3.4 (m, 12H), 1.8–1.3 (m, 10H) ppm.

EXAMPLE 13

By substituting the appropriate epoxide for methylenecyclohexane epoxide in the procedure of Example 12, the compounds in Table XV were prepared.

TABLE XV

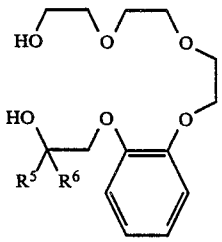

| $R^5$ and $R^6$; or $R^5R^6C=$ | Spectral Data |
|---|---|
| 4-t-butylcyclo-hexylidene | IR: 3425, 2950, 1600. NMR: 6.9 (s, 4H), 4.3–3.5 (m, 14H), 3.2 (s, 2H), 2.2–1.0 (m, 9H), 0.9 (s, 9H). |
| 4-chlorophenoxy-methyl; H | IR: 3400, 1601. NMR: 7.2 (d, 2H), 6.9 (m, 6H), 4.4–3.5 (m, 19H). |
| 3,3,5-trimethyl-cyclohexylidene | NMR: 6.9 (s, 4H), 4.3–3.5 (m, 14H), 3.3 (s, 2H), 2.1–1.5 (m, 4H), 1.5–0.8 (m, 12H). |
| 4-t-butylphenoxy-methyl; H | NMR: 7.3 (m, 2H), 6.8 (m, 6H), 4.3–3.6 (m, 19H), 1.4 (s, 9H). |
| phenoxymethyl; H | NMR: 7.4–7.1 (m, 2H), 6.9 (m, 7H), 4.3–3.5 (m, 19H). |
| thiophenoxymethyl; H | NMR: 7.2 (m, 5H), 6.8 (s, 4H), 4.3–3.4 (m, 17H), 3.2 (m, 2H). |

EXAMPLE 14

Reaction of 2-hydroxy-1-(2-[2-(2-[2-tetrahydropyranyloxy]ethoxy)ethoxy]ethoxy)-4-t-octylbenzene (contaminated with some of the corresponding 5-t-octyl isomer) with the appropriate epoxide, using the procedure of Example 12, afforded the compounds in Table XVI, in which R$^4$ is t-octyl.

TABLE XVI

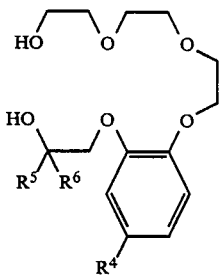

| $R^5$ and $R^6$; or $R^5R^6C=$ | Spectral Data |
|---|---|
| cyclohexylidene | NMR: 6.9 (m, 3H), 4.3–3.5 (m, 14H), 3.4 (bs, 2H), 1.6 (m, 12H), 1.3 (s, 6H), 0.8 (s, 9H). |
| hexyl; H | NMR: 6.9 (m, 3H), 4.3–3.5 (m, 17H), 1.7 (s, 2H), 1.4 (m, 16H), 0.9 (m, 3H), 0.8 (s, 9H). |
| 3,3,5-trimethylcyclo-hexylidene | NMR: 6.9 (m, 3H), 4.3–3.0 (m, 16H), 1.8–0.7 (m, 33H). |
| cycloheptylidene | NMR: 6.8 (m, 3H), 4.2–3.6 (m, 16H), 1.9–1.0 (m, 20H), 0.8 (s, 9H). |
| phenoxymethyl; H | NMR: 7.4–6.8 (m, 8H), 4.2–3.6 (m, 19H), 1.8 (s, 2H), 1.4 (s, 6H), 0.8 (s, 9H). |
| thiophenoxymethyl; H | NMR: 7.2 (m, 5H), 6.8 (m, 3H), 4.3–3.5 (m, 17H), 3.2 (m, 2H), 1.6 (s, 2H), 1.3 (s, 6H), 0.8 (s, 9H). |

EXAMPLE 15

The diols in Table XVII can be prepared by reaction of the appropriate catechol with 2-(2-[2-(2-chloroethoxy)ethoxy]ethoxy)tetrahydropyran according to the procedure of Preparation S, followed by reaction with the appropriate epoxide according to the procedure of Example 12.

TABLE XVII

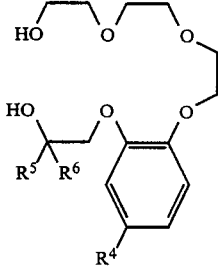

| R$^4$ | $R^5$ and $R^6$; or $R^5R^6C=$ |
|---|---|
| t-octyl | H; H |
| t-octyl | CH$_3$; H |
| CH$_3$ | n-octyl; H |
| isopropyl | cyclopentylidene |
| n-hexyl | cycloheptylidene |
| H | t-octyl; H |

PREPARATION A

2-Bromo-5-t-butyl-1,3-dimethylbenzene

To a solution of 200 g (1.23 mole) 5-t-butyl-1,3-dimethylbenzene and 83 ml (1.23 mole) propylene oxide in 500 ml of methylene chloride at 15° C. or less, 63 ml (1.23 mole) bromine was added dropwise while maintaining the solution temperature at 15° C. or less. The reaction mixture was allowed to warm to 25° C. overnight. A 200 ml solution of 5% by weight of potassium hydroxide in water was added and the resulting two phase system was stirred for 1 hr at 25° C. The organic phase was washed with water and dried over anhydrous magnesium sulfate. After solvent evaporation an oil was left which when crystallized from methanol gave 265 g (87% yield) of the title compound after drying in vacuo. The oil could also be purified by distilling at 61°-70° C. under a reduced pressure of 0.25 mm of mercury.

NMR (CDCl$_3$): 1.3 (s, 9H), 2.4 (s, 6H) and 7.0 (s, 2H).

PREPARATION B

4-t-Butyl-2,6-dimethylbenzoic Acid

To 72.9 g (3 moles) magnesium in 473 ml of diethyl ether was added a small portion taken from a solution of 482 g (2 moles) 4-t-butyl-2,6-dimethylbromobenzene in 86 ml (1 mole) 1,2-dibromoethane with stirring. When the Grignard reaction commenced, the remaining solution was added at a rate to maintain reflux with external cooling. Following addition, the reaction mixture was maintained at reflux overnight, cooled and poured over solid carbon dioxide. The reaction mixture was acidified to pH 1.5 with concentrated hydrochloric acid to give the title acid which was extracted into 500 ml of diethyl ether. Replacement of the ether by hexane gave the title compound as a white solid (261 g, 63% yield, m.p. 160°-64° C.). See *Journal of Organic Chemistry*, 23, 1161 (1950).

NMR (CDCl$_3$): 1.35 (S, 9H), 2.4 (s, 6H) and 7.01 (s, 2H) ppm.

PREPARATION C

Methyl 4-t-Butyl-2,6-dimethylbenzoate

To 50 g (0.26 moles) of 4-t-butyl-2,6-dimethylbenzoic acid in 250 ml methylene chloride was added 25 ml (0.34 mole) of thionyl chloride at 25° C. After stirring overnight at 25° C. the solvent and remaining thionyl chloride were evaporated in vacuo. The resulting white solid was dissolved in 50 ml tetrahydrofuran and added dropwise to 250 ml of methanol containing 2 ml of pyridine. After heating the reaction mixture to reflux for 30 minutes the solvents were evaporated in vacuo and the residue was dissolved in 200 ml ethyl acetate and 100 ml of water was added. The organic phase was separated and washed with 100 ml saturated aqueous sodium bicarbonate, 50 ml water and 25 ml brine; then dried over anhydrous magnesium sulfate and evaporated to an oil. The oil was distilled in vacuo at 104°-8° C. at 1.2 mm of mercury to obtain 43 g (81% yield) of the title compound.

NMR (CDCl$_3$): 1.3 (s, 9H), 2.4 (s, 6H), 3.9 (s, 3H) and 7.0 (s, 2H).

PREPARATION D

Methyl 2,6-di(Bromomethyl)-4-t-butylbenzoate

Methyl 4-t-butyl-2,6-dimethylbenzoate (22 g, 0.1 mole), 1,3-dibromo-5,5-dimethylhydantoin (31.5 g, 0.11 moles) and benzoyl peroxide (50 mg) in carbon tetrachloride (300 ml) were heated to reflux and irradiated with a 275 watt sun lamp. After 1.5 hours of irradiation at reflux the yellow color of the reaction mixture had been dispersed. The reaction mixture was cooled to 25° C. and the hydantoin was removed by filtering. The carbon tetrachloride was evaporated in vacuo. The desired material crystallized from petroleum ether to give 18.4 g, 49% yield, m.p. 99°-100° C., of the title compound.

NMR (CDCl$_3$): 1.35 (s, 9H), 4.0 (s, 3H), 4.6 (s, 4H) and 7.35 (s, 2H) ppm.

Methyl 2,6-di(bromomethyl)benzoate was prepared in analogous fashion, mp 76°-79° C.

NMR (CDCl$_3$): 7.4 (s, 3H), 4.6 (s, 4H) and 4.0 (s, 3H) ppm.

PREPARATION E

3-Methyl-5-(t-octyl)catechol

A mixture of 3-methylcatechol (56 g, 0.45 mole) and 10 drops of concentrated sulfuric acid was heated to 100° C. Di-isobutylene (2,4,4-trimethyl-2-pentene) (67 g, 0.6 mole) was added dropwise over a 15 min. period. After stirring at 100° C. for an additional 20 min., the temperture was raised to 130° C. and maintained at that temperature for 2 hours. The reaction mixture was allowed to cool to 50° C. and ethyl acetate (0.5 liter) was added. The resulting organic solution was washed 3 times with 500 ml of saturated aqueous sodium carbonate, once with 1N hydrochloric acid (0.2 liter), water (0.2 liter) and brine (0.1 liter). The organic solution was dried over anhydrous magnesium sulfate and treated with activated carbon. The solution was filtered and evaporated to an orange oil. Addition 150 ml petroleum ether gave a white solid of the title compound (76 g, 72% yield).

NMR (CDCl$_3$): 6.7 (s, 2H), 2.2 (s, 3H), 1.7 (s, 2H), 1.3 (s, 6H) and 0.8 (s, 9H) ppm. IR (CH$_2$Cl$_2$): 3530, 2950 and 1475 cm$^{-1}$.

PREPARATION F

3-Methyl-5-(3,3-dimethylbutanoyl)catechol

While 3-methylcatechol (11.5 g, 0.093 mole) was melted at 85° C., 3,3-dimethylbutanoyl chloride (25 g, 0.186 mole) was added dropwise over 15 min. The resulting mixture was heated to 110° C. for 1.5 hrs. to complete the reaction. The mixture was cooled to 30° C., then dissolved in 25 ml carbon disulfide at 30° C. containing 3-methylcatechol (11.5 g, 0.09 mole). The resulting solution was added dropwise to a stirred suspension of aluminum trichloride (62 g, 0.465 mole) in carbon disulfide (110 ml) at 40° C. Following addition, the reaction mixture was stirred for 1 hr. at 25° C., then heated to 80° C. and the carbon disulfide removed by distillation. After solvent removal, the residual material was heated to 140°-145° C. for 3.5 hrs. then cooled in an ice bath and quenched with 200 ml of a 1:1 mixture of concentrated hydrochloric acid and water. Diethyl ether (150 ml) was added and the layers were separated. The aqueous layer was extracted further with 150 ml of diethyl ether. The combined organic portions were washed with two 50 ml portions of water, two 50 ml portions of 5% weight to volume sodium bicarbonate, 50 ml water and 25 ml brine. The diethyl ether was evaporated to give a brown oil which crystallized from 100 ml petroleum ether to yield the product as a light yellow solid (16.5 g, 40% yield, m.p. 139°-43°).

NMR (CDCl$_3$): 7.3 (q, 2H), 2.7 (s, 2H), 2.3 (s, 3H) and 1.05 (s, 9H) ppm. IR (KBr disc): 3448, 3180, 2940, 1653 and 1595 cm$^{-1}$.

PREPARATION G

3-Morpholinomethyl-5-t-octylcatechol

To paraformaldehyde (40 g, 1.3 mole) in 100 ml isopropanol at 25° C. was added morpholine (88 ml) in 0.5 liter isopropanol. The reaction mixture was refluxed for 30 minutes to effect solution. To the solution, 4-t-octylcatechol (222 g, 1.0 mole) dissolved in 0.5 liter isopropanol was added dropwise while maintaining the solution temperature at 60° C. The reaction mixture was stirred at reflux overnight. The reaction was cooled to 25° C. and the solvent was removed in vacuo to give a white solid which was triturated with 750 ml petroleum ether and collected. Overall yield from two crops was 86%, 280 g.

NMR (CDCl$_3$): 8.0 (s, 2H), 6.9 (d, 1H), 6.5 (d, 1H), 3.7 (m, 6H), 2.5 (m, 4H) 1.6 (s, 2H), 1.3 (s, 6H) and 0.8 (s, 9H) ppm.

PREPARATION H

3-Thiophenoxymethyl-5-t-octylcatechol

A suspension of 3-morpholinomethyl-5-t-octylcatechol (564 g, 1.76 mole) and 193.4 g (1.76 mole) benzenethiol in 0.8 liter dimethylformamide was kept at 130° C. under a nitrogen atmosphere for 20 hours. The reaction mixture was cooled to 25° C. and diluted with 3,000 ml diethyl ether. The resulting solution was washed in turn with 3×1,000 ml water, 500 ml 10% hydrochloric acid, 500 ml water and 500 ml brine. The washed solution was dried over anhydrous magnesium sulfate and evaporated in vacuo to a yellow oil (548.9 g, 91% yield) of the title compound.

NMR (CDCl$_3$): 7.2 (m, 5H), 6.8 (d, 1H), 6.5 (d, 1H), 5.8 (bs, 2H), 4.1 (s, 2H), 1.6 (s, 2H), 1.2 (s, 6H) and 0.6 (s, 9H) ppm.

PREPARATION I

5-(3,3-Dimethylbutanoyl)-3-methyl-1,2-di(2-[2-(2-tetrahydropyranyloxy)ethoxy]ethoxy)benzene A solution of 3-methyl-5-(3,3-dimethylbutanoyl)catechol (12 g, 0.054 mole), 2-(2-[2-chloroethoxy]ethoxy)-tetrahydropyran (24.8 g, 0.119 mole) and potassium carbonate (16.6 g, 0.12 mole) in 100 ml dimethyformamide was stirred under a nitrogen atmosphere at 140° C. for 16 hours. The reaction mixture was cooled to 25° C. and 500 ml diethyl ether and 300 ml water were added. The layers were separated and the organic layer was washed with four 250 ml portions of water and 100 ml brine, dried over anhydrous magnesium sulfate and the solvent evaporated in vacuo. The resulting brown oil was purified by column chromatography over silica gel with 10% ethyl acetate—90% chloroform. The title compound was isolated as a yellow oil (13.5 g, 44% yield).

IR: 1670 cm$^{-1}$.

NMR (CDCl$_3$): 7.4 (s, 2H), 4.6 (s, 2H), 4.4–3.4 (m, 20H), 2.8 (s, 2H), 2.3 (s, 3H), 1.6 (m, 12H ) and 1.05 (s, 9H) ppm.

Reaction of the appropriate catechol with 2-(2-[2-chloroethoxy]ethoxy)tetrahydropyran, using the above procedure, afforded the products in Tables XVIII and XIX below.

TABLE XVIII

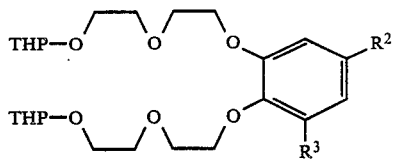

| R$^2$ | R$^3$ | Spectral Data |
|---|---|---|
| H | H | IR: 1590, 1500, 1250, 1125. NMR: 6.9 (s, 4H), 4.6 (m, 2H), 4.2–3.4 (m, 20H), 1.8–1.4 (m, 12H). |
| t-butyl | H | IR: 2940, 2860, 1530. NMR: 7.1 (m, 3H), 4.7 (m, 2H), 4.4–3.5 (m, 20H), 1.7 (m, 12H), 1.3 (s, 9H). |
| phenyl | H | IR: 2900, 2850, 1600. NMR: 7.6–6.8 (m, 8H), 4.6 (bs, 2H), 4.3–3.2 (m, 20H), 2.0–1.2 (m, 12H). |
| t-octyl | H | IR: 2900, 1510, 1460. NMR: 6.9 (m, 3H), 4.6 (s, 2H), 4.2–3.5 (m, 20H), 1.6 (m, 14H), 1.35 (s, 6H), 0.9 (s, 9H). |
| cyclohexyl | H | IR: 2920, 2850, 1510, 1450. NMR: 6.8 (m, 3H), 4.6 (s, 2H), 4.2–3.2 (m, 20H), 1.9–1.0 (m, 23H). |
| t-octyl | isopropyl | IR: 2950, 1450. NMR: 6.8 (m, 2H), 4.6 (s, 2H), 4.3–3.5 (m, 20H), 1.7 (m, 15H), 1.4 (s, 6H), 1.2 (d, 6H), 0.9 (s, 9H). |
| t-octyl | methyl | IR: 2950–2840, 1580. NMR: 6.9 (s, 2H), 4.7 (s, 2H), 4.3–3.4 (m, 20H), 2.3 (s, 3H), 1.7 (m, 14H), 1.3 (s, 6H), 0.8 (s, 9H). |
| t-butyl | morpholinomethyl | IR: 2950–2840, 1590. NMR: 6.9 (q, 2H), 4.6 (s, 2H), 4.3–4.1 (m, 4H), 4.1–3.5 (m, 20H), 2.5 (m, 4H), 1.7 (m, 12H), 1.3 (s, 9H). |
| H | methyl | IR: 2940, 2860. NMR: 6.7 (m, 4H), 4.6 (m, 2H), 4.2–3.4 (m, 20H), 2.2 (s, 3H), 1.8–1.4 (m, 12H). |
| t-butyl | isopropyl | IR: 2925–2825, 1560. NMR: 6.8 (m, 2H), 4.6 (s, 2H), 4.3–3.4 (m, 20H), 1.9–1.1 (m, 28H). |
| t-butyl | t-butyl | IR: 2940–2840. NMR: 6.9 (q, 2H), 4.6 (bs, 2H), 4.3–3.2 (m, 20H), 1.8–1.2 (m, 30H). |
| t-octyl | benzyl | IR: 3350, 2950–2850. |
| 4-t-butylphenyl | H | IR: 2950–2840, 1500. |
| methyl | methyl | IR: 2940, 2850, 1450. NMR: 6.8 (s, 2H), 4.7 (s, 2H), 4.3–3.3 (m, 20H), 2.2 (s, 6H), 1.8–1.4 (m, 12H). |
| t-octyl | morpholinomethyl | IR: 2925, 2850, 1600. NMR: 7.0 (q, 2H), 4.7 (s, 2H), 4.3–3.5 (m, 24H), 2.5 (m, 4H), 1.7 (m, 14H), 1.4 (s, 6H), 0.8 (s, 9H). |
| t-butyl | t-octyl | NMR: 6.9 (q, 2H), 4.6 (s, 2H), 4.3–3.4 (m, 20H), 1.9 (s, 2H), 1.6 (m, 12H), 1.5 (s, 6H), 1.3 (s, 9H), 0.8 (s, 9H). |
| 1-adamantyl | methyl | IR: 2925–2820. |
| t-octyl | 2-phenylethyl | IR: 2960, 2900. NMR: 7.2 (s, 5H), 6.7 (q, 2H), 4.6 (m, 2H), 4.3–3.5 (m, 20H), 2.9 (s, 4H), 1.6 (m, 14H), 1.2 (s, 6H), 0.7 (s, 9H). |
| t-octyl | 2-(4-methylphenyl)ethyl | IR: 2950–2875. |
| t-octyl | 3-phenylpropyl | IR: 2960–2850. |

TABLE XVIII-continued

[Structure: THP—O and THP—O connected via crown ether chains to benzene ring with R² and R³ substituents]

| R² | R³ | Spectral Data |
|---|---|---|
| t-octyl | 2-(2-fluoro-phenyl)ethyl | IR: 2950–2850. |
| t-octyl | 2-(2-methyl-phenyl)ethyl | IR: 2950–2860, 1590. |
| t-octyl | 2-(3-methyl-phenyl)ethyl | IR: 2960–2860. |
| t-octyl | 2-(4-t-butyl-phenyl)ethyl | IR: 2950–2850. |

TABLE XIX

[Structure: THP—O crown ether with benzene ring bearing t-octyl group and CH₂—S—aryl with R¹³ and R¹⁴]

| R¹³ and R¹⁴ | Spectral Data |
|---|---|
| 2-methoxy; H | IR: 2975–2850, 1580. NMR: 7.3–6.7 (m, 6H), 4.6 (m, 2H), 4.2–3.5 (m, 25H), 1.7 (m, 14H), 1.4 (s, 6H), 0.8 (s, 9H). |
| 3-methyl; H | IR: 2975–2875, 1590. NMR: 7.2–6.7 (m, 6H), 4.6 (m, 2H), 4.2–3.4 (m, 22H), 2.3 (s, 3H), 1.6 (m, 14H), 1.3 (s, 6H), 0.7 (s, 9H). |
| 3-methoxy; H | NMR: 7.2–6.6 (m, 6H), 4.6 (m, 2H), 4.4–3.4 (m, 25H), 1.6 (m, 14H), 1.3 (s, 6H), 0.7 (s, 9H). |
| 4-methoxy; H | NMR: 7.2 (m, 2H), 6.7 (m, 4H), 4.6 (m, 2H), 4.3–3.4 (m, 25H), 1.7 (m, 14H), 1.3 (s, 6H), 0.7 (s, 9H). |
| 2-bromo; H | NMR: 7.6–6.8 (m, 6H), 4.6 (m, 2H), 4.4–3.5 (m, 22H), 1.7 (m, 14H), 1.4 (s, 6H), 0.8 (s, 9H). |
| 4-bromo; H | NMR: 7.2 (m, 4H), 6.7 (m, 2H), 4.6 (m, 2H), 4.3–3.4 (m, 22H), 1.6 (m, 14H), 1.2 (s, 6H), 0.7 (s, 9H). |
| 4-fluoro; H | NMR: 7.4–6.7 (m, 6H), 4.6 (m, 2H), 4.3–3.5 (m, 22H), 1.6 (m, 14H), 1.2 (s, 6H), 0.6 s, 9H). |
| 4-t-butyl; H | IR: 2975–2860. NMR: 7.3 (s, 4H), 6.8 (m, 2H), 4.6 (m, 2H), 4.3–3.5 (m, 22H), 1.6 (m, 14H), 1.3 (d, 15H), 0.7 (s, 9H). |
| 2,6-dichloro | NMR: 7.2 (m, 5H), 4.6 (m, 2H), 4.4–3.5 (m, 22H), 1.8 (m, 14H), 1.4 (s, 6H), 0.8 (s, 9H). |

PREPARATION J

COMPOUND III (R is ethyl; R¹ is t-butyl; R² is 3,3-dimethylbutanoyl; R³ is methyl)

Sodium hydride (50% in oil, 1.27 g, 0.027 moles) was washed with two 25 ml portions of petroleum ether under nitrogen at 25° C. The majority of the petroleum ether was decanted to remove the oil. Tetrahydrofuran (75 ml) was added and the suspension was heated to reflux. A solution of ethyl 2,6-di(bromomethyl)-4-t-butylbenzoate (3.25 g, 0.0083 moles) and the title diol of Example 6 (3.3 g, 0.0083 moles) in 75 ml tetrahydrofuran was added dropwise over 2 hours at reflux under nitrogen. After 0.75 hour of additional reflux, the reaction was stirred at 25° C. for 48 hours. A 4:1 by volume mixture of tetrahydrofuran and water was added, followed by 50 ml of 1N HCl. The tetrahydrofuran was removed in vacuo and the aqueous residue extracted with 100 ml methylene chloride. The extract was dried over anhydrous magnesium sulfate and evaporated in vacuo to an organge oil (5 g). The title product was obtained by chromatography over silica gel with 90% chloroform—10% ethyl acetate as a colorless oil (2.5 g, 48% yield).

NMR (CDCl₃): 7.3 (s, 4H), 4.9–4.0 (m, 10H), 4.0–3.4 (m, 12H), 2.8 (s, 2H), 2.3 (s, 3H), 1.4 (s and t, 12H) and 1.1 (s, 9H) ppm. IR: 1730 and 1660 cm⁻¹.

PREPARATION K

Reaction of the appropriate alkyl 2,6-di(bromomethyl)benzoate of formula X with the requisite diol of formula XI in the presence of sodium hydride, using the procedure of Preparation J, affords the compounds in Tables XX, XXI, XXII and XXIII.

TABLE XX

[Structure: Bis-crown ether linked through two benzene rings; one bearing R¹ and COOCH₃, the other bearing R² and R³]

| R¹ | R² | R³ | Yield (%) |
|---|---|---|---|
| H | H | H | 20 |
| H | t-butyl | H | 25 |
| H | phenyl | H | 13 |
| H | t-octyl | H | 28 |
| H | cyclohexyl | H | 30 |
| H | t-octyl | isopropyl | 40 |
| H | t-octyl | methyl | 44 |
| H | t-butyl | morpholino-methyl | 23 |
| H | t-octyl | thiophenxoy-methyl | 28 |
| H | n-octyl | H | 32 |
| H | n-undecyl | H | 25 |
| t-butyl | t-butyl | H | 96 |
| t-butyl | t-octyl | H | 66 |
| t-butyl | n-octyl | H | 29 |
| t-butyl | n-undecyl | H | 41 |
| t-butyl | H | methyl | 30 |
| t-butyl | t-octyl | methyl | 50 |
| t-butyl | t-octyl | isopropyl | 65 |
| t-butyl | t-butyl | isopropyl | 23 |
| t-butyl | t-butyl | t-butyl | 30 |
| t-butyl | t-octyl | benzyl | 50 |
| t-butyl | 4-t-butyl-phenyl | H | 60 |
| t-butyl | 4-t-butyl-phenyl | t-butyl | 25 |
| t-butyl | t-butyl | morpholino-methyl | 11 |
| t-butyl | t-octyl | morpholino-methyl | 30 |
| t-butyl | methyl | t-octyl | 52 |
| t-butyl | t-butyl | t-octyl | 41 |
| t-butyl | 1-adamantyl | methyl | 25[1] |
| t-butyl | t-octyl | 2-phenyl-ethyl | 37 |

TABLE XX-continued

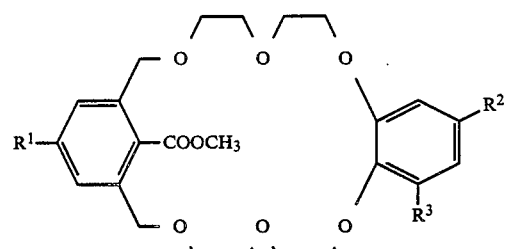

| R$^1$ | R$^2$ | R$^3$ | Yield (%) |
|---|---|---|---|
| t-butyl | t-octyl | 2-(4-tolyl)-ethyl | 58 |
| t-butyl | t-octyl | 3-phenyl-propyl | 23 |
| t-butyl | t-octyl | 2-(2-fluorophenyl)ethyl | 43 |
| t-butyl | t-octyl | 2-(2-tolyl)-ethyl | 26 |
| t-butyl | t-octyl | 2-(3-tolyl)-ethyl | 45 |
| t-butyl | t-octyl | 2-(4-t-butylphenyl)ethyl | 92 |

[1]Corresponding ethyl ester used.

TABLE XXI

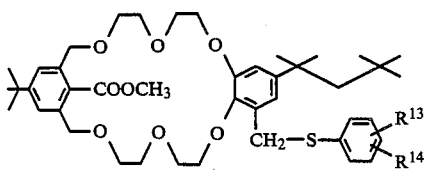

| R$^{13}$ and R$^{14}$ | Yield (%) |
|---|---|
| 2-methoxy; H | 28 |
| 3-methyl; H | 37 |
| 3-methoxy; H | 38 |
| 4-methoxy; H | 36 |
| 2-bromo; H | 34 |
| 4-bromo; H | 34 |
| 4-fluoro; H | 41 |
| 2-chloro; H | 31 |
| 3-chloro; H | 49 |
| 4-t-butyl; H | 35 |
| 2,6-dichloro | 30 |

TABLE XXII

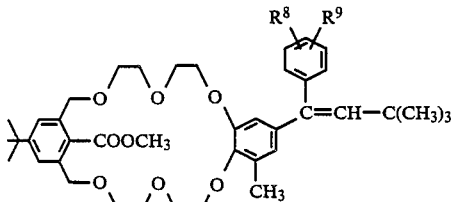

| R$^7$ and R$^8$ | Yield (%) |
|---|---|
| H, H | 40 |
| 4-methylthio; H | 33 |
| 2-methyl; H | 62 |
| 3-methoxy; H | 32 |
| 4-methoxy; H | 14 |
| 2,6-dimethyl | 49 |
| 2,6-dimethoxy | 35 |
| 2-ethyl; H | 32 |
| 2-methoxy; H | 49 |
| 2-methylthio; H | 24 |
| 3,5-dimethyl | 17 |

TABLE XXII-continued

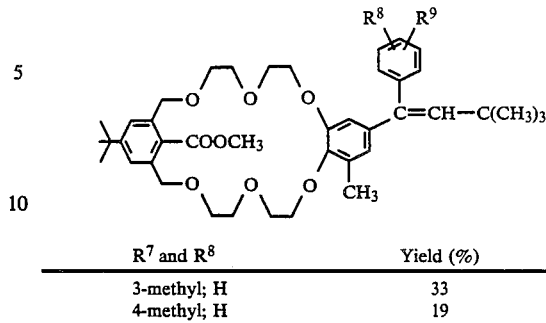

| R$^7$ and R$^8$ | Yield (%) |
|---|---|
| 3-methyl; H | 33 |
| 4-methyl; H | 19 |

TABLE XXIII

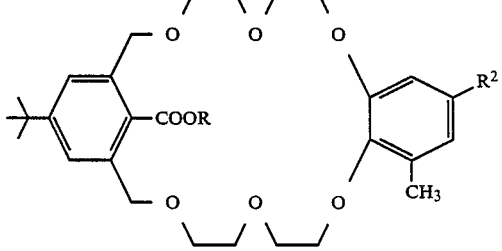

| R | R$^2$ | Yield (%) |
|---|---|---|
| CH$_2$CH$_3$ | 1-(n-butyl)-3,3-dimethylbutyl | 37 |
| CH$_2$CH$_3$ | 1-(n-hexyl)-3,3-dimethylbutyl | 37 |
| CH$_2$CH$_3$ | 1-phenyl-3,3-dimethylbutyl | 36 |
| CH$_2$CH$_3$ | 1-(n-octyl)-3,3-dimethylbutyl | 49 |
| CH$_2$CH$_3$ | 1-(isoamyl)-3,3-dimethylbutyl | 28 |
| CH$_2$CH$_3$ | 1-ethyl-3,3-dimethylbutyl | 24 |
| CH$_2$CH$_3$ | 1-(4-tolyl)-3,3-dimethylbutyl | 23 |
| CH$_2$CH$_3$ | 1-(2-tolyl)-3,3-dimethylbutyl | 43 |
| CH$_2$CH$_3$ | 1-(2-methoxyphenyl)-3,3-dimethylbutyl | 42 |
| CH$_3$ | 1-(4-methylthiophenyl)-3,3-dimethylbutyl | 15 |
| CH$_3$ | 1-(4-methoxyphenyl)-3,3-dimethylbutyl | 27 |

PREPARATION L

COMPOUND VIII (R is methyl; R$^1$ is t-butyl; R$^2$ is t-octyl; R$^3$ is acetoxymethyl)

Compound VIII (R is methyl; R$^1$ is t-butyl; R$^2$ is t-octyl; R$^3$ is morpholinomethyl) (3.6 g) was dissolved in 10 ml of acetic anhydride and kept at reflux for 18 hours. The reaction was cooled to 25° C. and a portion of the unreacted acetic anhydride was removed in vacuo. Water (10 ml) was added to the reaction mixture and the mixture was stirred for 2 hours at 25° C. to hydrolyze any remaining acetic anhydride. The aqueous layer was extracted with three 25 ml portions of diethyl ether. The ethereal extracts were combined and washed with 40 ml 5% weight-to-volume of aqueous sodium bicarbonate, dried over anhydrous magnesium sulfate and evaporated in vacuo to give a brown oil. The title compound was isolated by column chromatography of the brown oil over silica gel with 90% chloroform—10% ethyl acetate as an oil (2 g, 54% yield).

IR: 1730 cm$^{-1}$.

NMR (CDCl$_3$): 7.4 (s, 2H), 7.0 (s, 2H), 5.2 (s, 2H), 4.6 (s, 4H), 4.4–3.5 (m, 19H), 2.1 (s, 3H), 1.8 (s, 2H), 1.4 (s, 15H) and 0.8 (s, 9H) ppm.

PREPARATION M

COMPOUND VIII (R is methyl; $R^1$ is t-butyl; $R^2$ is t-octyl; $R^3$ is hydroxymethyl)

The product of Preparation L (2 g, 0.0029 mole) was dissolved in methanol (35 ml) containing 5 ml of 5% weight-to-volume aqueous potassium hydroxide. The solution was stirred at 25° C. for two hours, at which time thin layer chromatography showed no starting material, only one more polar product. The methanol was evaporated in vacuo and the aqueous residue was extracted with two 50 ml portions of diethyl ether. The ether extracts were combined and washed with 20 ml brine and dried over anhydrous magnesium sulfate. Evaporation of the solvent gave the title product as a colorless oil (1.51 g, 81% yield).

IR: 3400 and 1725 $cm^{-1}$.

NMR (CDCl$_3$): 7.3 (s, 2H), 6.8 (s, 2H), 4.5 (d, 6H), 4.2–3.4 (m, 19H), 1.6 (s, 2H), 1.3 (s, 15H) and 0.77 (s, 9H) ppm.

PREPARATION N

COMPOUND VIII (R is methyl; $R^1$ is t-butyl; $R^2$ is t-octyl; $R^3$ is methoxymethyl)

The product of Preparation M (1.5 g, 0.0023 moles) was dissolved in 40 ml of tetrahydrofuran and added dropwise to a suspension of sodium hydride (0.170 g, 0.00345 moles, 50% in oil) in tetrahydrofuran (30 ml) at 25° C. After addition (5 min), a solution of dimethyl sulfate (1 ml, 0.01 moles) in dimethylformamide (16 ml) was added at ;b 25° C. The resulting reaction mixture was refluxed for 18 hours. The reaction mixture was cooled to 25° C. and 100 ml of diethyl ether was added. The resulting mixture was washed with three 20 ml portions of water followed by 20 ml of brine. The organic layer was dried over anhydrous magnesium sulfate. Evaporation of the solvents gave 1.1 g (73% yield) of the title compound as a colorless oil which showed one spot by thin layer chromatography.

IR: 1725 $cm^{-1}$.

NMR (CDCl$_3$): 7.3 (s, 2H), 6.9 (d, 2H), 4.6 (m, 6H), 4.3–3.3 (m, 22H), 1.7 (s, 2H), 1.4 (s, 15H) and 0.8 (s, 9H) ppm.

HRMS: M+ (658.3920) $C_{38}H_{58}O_9$.

The above procedure was repeated, except that the dimethyl sulfate was replaced by benzyl bromide, 2-methylbenzyl bromide and 4-methylbenzyl bromide. This afforded the following compounds:

COMPOUND VIII (R is methyl; $R^1$ is t-butyl; $R^2$ is t-octyl; $R^3$ is benzyloxymethyl) (86% yield), COMPOUND VIII (R is methyl; $R^1$ is t-butyl; $R^2$ is t-octyl; $R^3$ is 2-methylbenzyloxymethyl) (56% yield) and COMPOUND VIII (R is methyl; $R^1$ is t-butyl; $R^2$ is t-octyl; $R^3$ is 4-methylbenzyloxymethyl) (85% yield), respectively.

PREPARATION O

COMPOUND VIII (R is methyl; $R^1$ is t-butyl; $R^2$ is t-octyl; $R^3$ is phenoxmethyl)

To a stirred solution of the product of Preparation M (1.5 g), phenol (0.25 g) and triphenylphosphine (0.7 g) in dry tetrahydrofuran (50 ml) was added diethyl axodicarboxylate (0.42 ml), and the reaction mixture was stirred under nitrogen for 48 hours. The tetrahydrofuran was removed by evaporation and a mixture of 10 ml of diethyl ether and 20 ml of petroleum ether was added. The precipitate was removed by filtration and the filtrate was washed with 5% potassium hydroxide, followed by water, followed by brine. The washed filtrate was then evaporated in vacuo and the residue was purified by column chromatography on silica gel to give 748 mg (48% yield) of the title compound.

IR (neat): 1730 $cm^{-1}$.

NMR (CDCl$_3$): 7.3–6.7 (m, 9H), 5.1 (s, 2H), 4.6 (s, 4H), 4.2L–3.5 (m, 19H), 1.6 (s, 2H), 1.35 (s, 15H), 0.7 (s, 9H) ppm.

The corresponding compounds in which $R^3$ is 4-methylthiopheoxmethyl, 4-acetylpheenoxmethyl and 2-acetylphenoxmethyl were prepared in 43, 21 and 60% yields, respectively, by the above procedure but using the appropriately-substituted phenol.

PREPARATION P

COMPUND VIII (R is methyl $R^1$ is t-butyl; $R^2$ is t-octyl; $R^3$ is bromomethyl)

The title compound of Preparation M (1.32 g, 0.002 moles) was dissolved in 25 ml toluene and treated at 0° C. with phosphorous tribromide (0.1 ml) followed by stirring at 0° C. for 1.5 hours. Diethyl ether (50 ml) was added and the reaction mixture washed with 25 ml 5% weight-to-volume aqueous sodium bicarbonate, 25 ml brine and dried over anhydrous magnesium sulfate. The solvent was evaporated to yield an oil of the title compound (1.08 g, 75% yield).

IR: 1730 $cm^{-1}$.

No hydroxyl absorbance lines were present.

PREPARATION Q

COMPOUND VIII (R is methyl; $R^1$ is t-butyl; $R^2$ is t-octyl; $R^3$ is 2-pyridylthiomethyl)

The title compound of Preparation P (1.0 g, 0.0015 mole) was dissolved in 40 ml chloroform and added to 2-mercaptopyridine dissolved in chloroform (15 ml) at 25° C. The reaction mixture became cloudy following the addition and then it was refluxed overnight. The reaction mixture was washed with 10 ml 1N potassium hydroxide, 10 ml 1N hydrochloric acid, 10 ml brine and dried over anhydrous magnesium sulfate. The chloroform was removed in vacuo to give an oil. The title compound was isolated by column chromatography over silica gel with 90% chloroform—10% ethyl acetate (0.84 g, 57% yield).

IR: 1730 $cm^{-1}$.

NMR (CDCl$_3$): 8.4 (d, 1H), 7.4–6.6 (m, 7H), 4.6 (s, 4H), 4.4 (s, 2H), 4.2–3.4 (m, 19H), 1.6 (s, 2H), 1.4 (m, 15H) and 0.6 (s, 9H) ppm.

PREPARATION R

Reaction of the product of Preparation P with the appropriate thiol of the formula HS-$C_6H_3R^{13}R^{14}$ and 1 molar equivalent of a tertiary amine (usually triethylamine), using the procedure of Preparation Q, afforded the compounds in Table XXIV.

TABLE XXIV

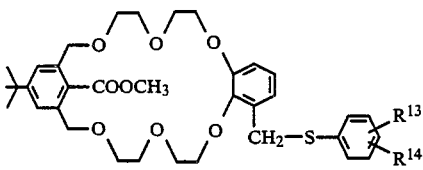

| R13 and R14 | Yield (%) |
| --- | --- |
| 2,6-dimethyl | 35 |
| 2-ethyl; H | 24 |
| 2,3-dimethyl | 26 |
| 3-trifluoromethyl; H | 31 |
| 4-hydroxy; H | 64 |
| 4-methylthio; H | 45 |

PREPARATION S

1-Hydroxy-2-(2-(2-hydroxyethoxy)ethoxy]ethoxy)benzene

Catechol (22 g, 0.2 mole), 2-(2-[2-(2-chloroethoxy)ethoxy]ethoxy)tetrahydropyran (50.5 g, 0.2 mole) and potassium carbonate (27.6 g, 0.2 moles) were combined in dimethylformamide (250 ml) and heated under a nitrogen atmosphere at 140° C. for 18 hours. The reaction mixture was cooled to 30° C. and poured into 500 ml water at 25° C. The aqueous mixture was extracted with 1000 ml of a mixture of diethyl ether (3 parts by volume ) and methylene chloride (1 part by volume). The organic extract was washed with 400 ml water (4 times); then evaporated in vacuo to a brown oil. This oil was taken up in 250 ml methanol and treated with 25 ml 1N hydrochloric acid for 2 hrs at 25° C. to remove the tetrahydropyran protecting group. The methanol was evaporated in vacuo and the aqueous residue extracted with 250 ml methylenechloride. The desired product was extracted from the methylene chloride extract into 10% weight-to-volume of potassium hydroxide in water (150 ml). The basic extract was acidified with 6N HCl and extracted with 250 ml methylene chloride. Evaporation gave a brown oil which was distilled in vacuo at 170°-173° at 0.07 mm of mercury.

NMR (CDCL$_3$): 7.7 (s, 1H), 6.9 (m, 4H) and 4.2–3.5 (m, 12H) ppm.

Repetition of the above procedure, but using 4-t-octylcatechol, afforded 2-hydroxy-1-(2-[2-(2-[2-tetrahydropyranyloxy]ethoxy)ethoxy]ethoxy)-4-t-octylbenzene, contaminated with the corresponding 5-t-octyl isomer.

NMR: 6.8 (m, 3H), 4.2–3.6 (m, 14H), 1.6 (s, 2H), 1.4 (s, 6H), 0.8 (s, 9H).

PREPARATION T

COMPOUND IX (R is methyl R$^1$ is t-butyl; R$^4$ is hydrogen; R$^5$ and R$^6$ form cyclohexylidene ring)

The title compound was prepared according to the procedure of Preparation J using 1-([1-hydroxycyclohexyl]methoxy)-2-(2-[2-(2-hydroxyethoxy)ethoxy]ethoxy)benzene (4.17 g, 0.0118 mole), methyl, 2,6-di(-bromomethyl)-4-t-butylbenzoate (4.7 g, 0.012 mole) and sodium hydride (50% in oil, 1.25 g, 0.026 mole) as the starting materials. The title compound was isolated as an oil by column chromatography over 200 g silica gel eluted with 90% chloroform—10% ethyl acetate (4.5 g, 67% yield).

IR: 1725 cm$^{-1}$.

NMR (CDCl$_3$): 7.5 (d, 1H), 7.2 (d, 1H), 6.9 (s, 4H), 4.8 (s, 2H), 4.6 (s, 2H), 4.1–3.4 (m, 17H), 1.6 (m, 10H) and 1.3 (s, 9H) ppm.

HRMS: m/e 57.03208 (C$_{33}$H$_{46}$O$_8$, m+), (base peak).

PREPARATION U

Reaction of the appropriate diol with methyl 2,6-di(-bromomenthyl)-4-t-butylbenzoate in the presence of sodium hydride, using the procedure of Preparation J, afforded the compounds in Table XXV.

TABLE XXV

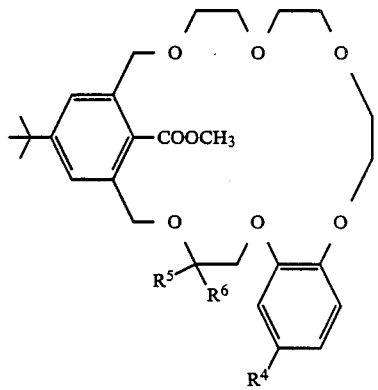

| R$^4$ | R$^5$ and R$^6$; or R$^5$R$^6$C = | Yield (%) |
| --- | --- | --- |
| H | 4-t-butylcyclohexylidene | 52 |
| H | 4-chlorophenoxymethyl; H | 41 |
| H | 3,3,5-trimethylcyclohexylidene | 46 |
| H | 4-t-butylcyclohexylidene | 55 |
| H | phenoxymethyl; H | 64 |
| H | thiophenoxymethyl; H | 83 |
| t-octyl | cyclohexylidene | 11 |
| t-octyl | n-hexyl; H | 19 |
| t-octyl | 3,3,5-trimethylcyclohexylidene | 37 |
| t-octyl | cycloheptylidene | 14 |
| t-octyl | phenoxymethyl; H | 47 |
| t-octyl | thiophenoxymethyl; H | 42 |

PREPARATION V 2-(2-[2-(2-Hydroxyethoxy)ethoxy]ethoxy)5-t-octylbenzaldehyde

A mixture of methyl 5-t-octylsalicylate (37.7 g, 0.143 mole), 2-(2-[2-(2-chloroethoxy)ethoxy]ethoxy)tetrahydropyran (54 g, 0.124 mole), potassium carbonate (28 g, 0.217 mole) and N,N-dimethylformamide (250 ml) was heated at 140° C., under nitrogen, for 18 hours, with stirring. The mixture was cooled, diluted with ether, and then washed liberally with saturated sodium chloride solution. The ethereal solution was dried (MgSO$_4$) and evaporated in vacuo to give an oil, which was chromatographed on silica gel to give 46 g of methyl 2-(2-[2-(2-[2-tetrahydropyranyloxy]ethoxy)ethoxy]ethoxy)-5-octylsalicylate.

The latter ester (46 g, 0.096 mole) was dissolved in a small amount of dry tetrahydrofuran, and the solution was added to a slurry of lithium aluminum hydride (3 g, 0.075 mole) in tetrahydrofuran. The mixture was heated under reflux for 18 hours and then cooled. To the cooled mixture was added aqueous tetrahydrofuran, dropwise, followed by saturated sodium sulfate, followed by solid sodium sulfate. The resulting mixture was filtered and the filtrate was evaporated in vacuo to give 39.6 g (91% yield) of 2-(2-[2-(2-[2-tetrahydropyranyloxy]ethoxy)ethoxy]ethoxy)-5-t-octylbenzyl alcohol as an oil.

The above benzyl alcohol (39.6 g, 0.088 mol) in dichloromethane (150 ml) was added dropwise to a suspension of pyridinium dichromate (45.5 g, 0.13 mole, *Tetrahderon Letters,* 399 [1979]) in dichloromethane (250 ml), with stirring. Stirring was continued overnight, and then the reaction mixture was diluted with ether and filtered through a magnesium sulfatesilica gel pad. The filtrate was washed with 1N hydrochloric acid and then it was evaporated in vacuo to give 35.6 g (90% yield) of 2-(2-[2-(2-[2-tetrahydropyranyloxy]ethoxy)ethoxy]ethoxy )-5-octylbenzaldephyde, as an oil.

The above benzaldehyde was dissolved in methanol (400 ml) containing 1N hydrochloric acid (50 ml) and the mixture was stirred at room temperature for 3 hours. The methanol was removed by evaporation in vacuo, and the residue was extracted with dichloromethane. The extracts were evaporated in vacuo, to give the title compound as an oil (27.2 g).

PREPARATION W 2-(2-[2-(2-Hydroxyethoxy)ethoxy]ethoxy)-5-t-octyl-phenoxy Formate

The product of Preparation V (27.2 g, 0.074 mole) in dichloromethane (300 ml) was added to a solution of 3-chloroperbenzoic acid (22.3 g, 0.11 mole) in dichloromethane (200 ml) during 1 hour. The reaction mixture was stored at room temperature for 18 hours and then it was heated under reflux for 5 hours. The reaction mixture was cooled to ca 0° C. and filtered. The volume of the filtrate was reduced to ca 50 ml and then ether was added. The resulting mixture was washed with sodium bicarbonate solution, sodium bisulfite solution and sodium chloride solution. The ethereal solution was then dried (MgSO$_4$) and evaporated in vacuo to give the title compound as an oil.

PREPARATION X 2-(2-[2-(2-Hydroxyethoxy)ethoxy]ethoxy)-5-t-octyl-phenol

The product of Preparation W was dissolved in methanol (400 ml) containing concentrated hydrochloric acid (4 ml) and the mixture was heated under reflux for 4 hours. The methanol was removed by evaporation in vacuo and the residue was dissolved in ethyl acetate. The ethyl acetate solution was dried (MgSO$_4$) and then it was concentrated to ca 50 ml. Petroleum ether (400 ml) was added and the resulting mixture was cooled. The solid was recovered by filtration to give 7.2 g (28% yield) of the title compound as a white crystalline solid.

NMR (CDCl$_3$): 6.9 (m, 3H), 4.1 (m, 2H), 3.9–3.5 (m, 12H), 1.6 (s, 2H), 1.3 (s, 6H) and 0.8 (s, 9H) ppm.

I claim:

1. A macrocyclic polyether compound of formula

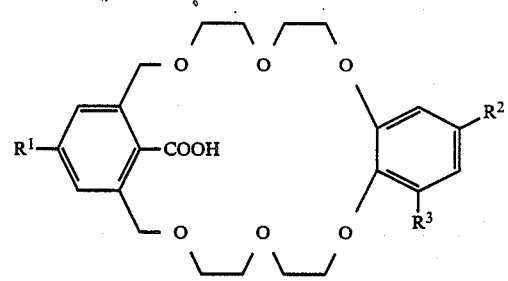

and the pharmaceutically-acceptable base salts thereof, wherein:

R$^1$ is selected from the group consisting of hydrogen and t-butyl;

R$^2$ is selected from the group consisting of hydrogen, alkyl having 1 to 14 carbons, cycloalkyl having 5 to 8 carbons, phenyl, alkylphenyl having 1 to 4 carbons in said alkyl, 1-adamantyl, —C(R$^7$)=CH—C(CH$_3$)$_3$,

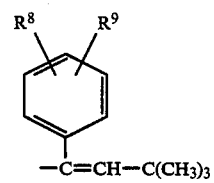 and 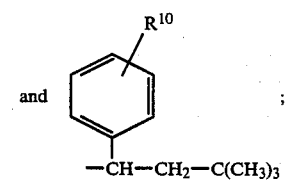 ;

wherein R$^7$ is hydrogen or alkyl having 1 to 8 carbons; R$^8$ and R$^9$ when taken separately are each hydrogen, alkyl having 1 to 3 carbons, alkoxy having 1 to 3 carbons or alkylthio having 1 to 3 carbons; R$^8$ and R$^9$ when taken together with the carbons to which they are attached form a fused benzo ring; and R$^{10}$ is hydrogen, alkyl having 1 to 3 carbons, alkoxy having 1 to 3 carbons or alkylthio having 1 to 3 carbons;

R$^3$ is selected from the group consisting of hydrogen, alkyl having 1 to 8 carbons, hydroxymethyl, methoxymethyl,

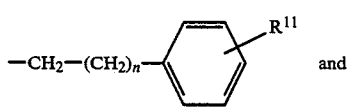 and

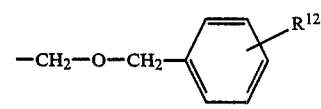

wherein R$^{11}$ is hydrogen, alkyl having 1 to 3 carbons, fluoro or chloro; R$^{12}$ is hydrogen, alkyl having 1 to 3 carbons or alkylthio having 1 to 3 carbons; and n is an integer from 0 to 3;

provided that when R$^3$ is said

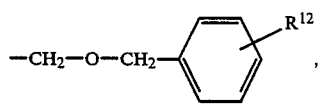 ,

R$^2$ must be t-octyl.

2. A compound according to claim 1, wherein $R^3$ is selected from the group consisting of hydrogen, alkyl having 1 to 8 carbons, hydroxymethyl, methoxymethyl, said

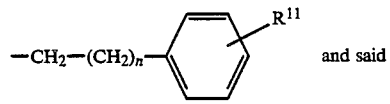 and said

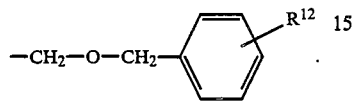

3. A compound according to claim 2, wherein $R^1$ is t-butyl.

4. A compound according to claim 3, wherein $R^2$ is t-octyl and $R^3$ is hydrogen or said alkyl.

5. A compound according to claim 4, wherein $R^3$ is methyl.

6. A compound according to claim 3, wherein $R^2$ is said $-C(R^7)=CH-C(CH_3)_3$ or said

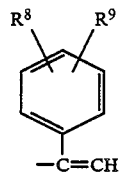

and $R^3$ is said alkyl.

7. A compound according to claim 6, wherein $R^2$ is $-CH=CH-C(CH_3)_3$ and $R^3$ is methyl.

8. A compound according to claim 6, wherein $R^2$ is

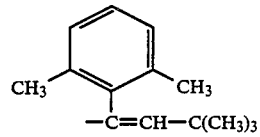

and $R^3$ is methyl.

9. A method of increasing the efficiency of feed utilization in ruminant animals which comprises administering orally to said animals an effective propionate-increasing amount of a macrocyclic polyether compound according to claim 1.

10. The method according to claim 9, wherein said ruminant animals are cattle.

* * * * *